(12) United States Patent
Matsuoka et al.

(10) Patent No.: US 8,262,678 B2
(45) Date of Patent: Sep. 11, 2012

(54) CLIP PACKAGE FOR CLIP APPLICATION APPARATUS

(75) Inventors: Yoshiaki Matsuoka, Saitama (JP); Yoshiyuki Kunuki, Saitama (JP)

(73) Assignee: Fujifilm Corporation, Tokyo (JP)

( * ) Notice: Subject to any disclaimer, the term of this patent is extended or adjusted under 35 U.S.C. 154(b) by 419 days.

(21) Appl. No.: 12/544,622

(22) Filed: Aug. 20, 2009

(65) Prior Publication Data
US 2010/0049217 A1 Feb. 25, 2010

(30) Foreign Application Priority Data

Aug. 21, 2008 (JP) ................ 2008-213105
Aug. 21, 2008 (JP) ................ 2008-213106
Aug. 21, 2008 (JP) ................ 2008-213118

(51) Int. Cl.
*A61B 17/10* (2006.01)

(52) U.S. Cl. .............. 606/142; 606/139; 606/151

(58) Field of Classification Search ............. 606/139, 606/142, 143, 151, 157, 158; 206/338, 339
See application file for complete search history.

(56) References Cited

U.S. PATENT DOCUMENTS

| 5,531,763 | A | * | 7/1996 | Mastri et al. ............... 606/148 |
| 6,319,258 | B1 | * | 11/2001 | McAllen et al. ............ 606/104 |
| 6,814,742 | B2 | | 11/2004 | Kimura et al. |
| 2006/0058818 | A1 | * | 3/2006 | Liberatore et al. .......... 606/142 |
| 2009/0275959 | A1 | * | 11/2009 | Cui et al. .................... 606/143 |
| 2009/0318937 | A1 | * | 12/2009 | Matsuoka et al. ........... 606/143 |

FOREIGN PATENT DOCUMENTS

JP 2002-191609 A 7/2002

* cited by examiner

*Primary Examiner* — Darwin Erezo
*Assistant Examiner* — Alexander Orkin
(74) *Attorney, Agent, or Firm* — Birch, Stewart, Kolasch & Birch, LLP

(57) ABSTRACT

A multiple hemostatic clip application apparatus operates for tissue clamping in combination with an endoscope. For use with the clip application apparatus, a clip package is provided, and has a multiple clip assembly, which includes a clip device, and a fastening mechanism, disposed at a proximal end of the clip device, for fastening to a shaft head of an operating wire inserted through a flexible sheath of the clip application apparatus. A coupling device includes a casing for containing the multiple clip assembly in a manner movable from the fastening mechanism toward the flexible sheath, and a guide slider for pressing the shaft head toward the fastening mechanism, for fastening together. The fastening mechanism emerges from the casing, the shaft head being overlapped on the fastening mechanism in an axial direction of the multiple clip assembly.

19 Claims, 21 Drawing Sheets

FIG. 2A
FIG. 2B
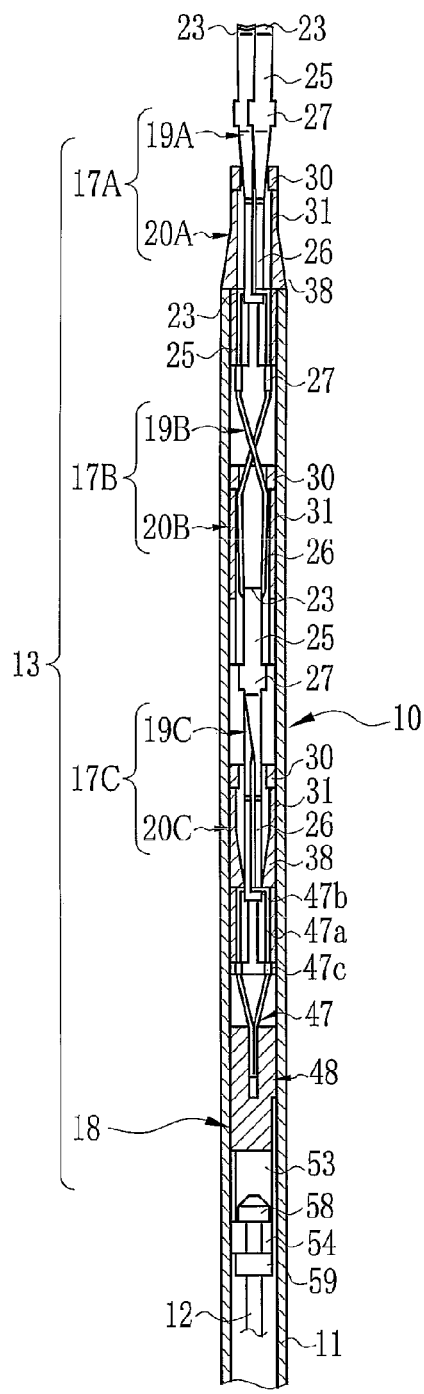
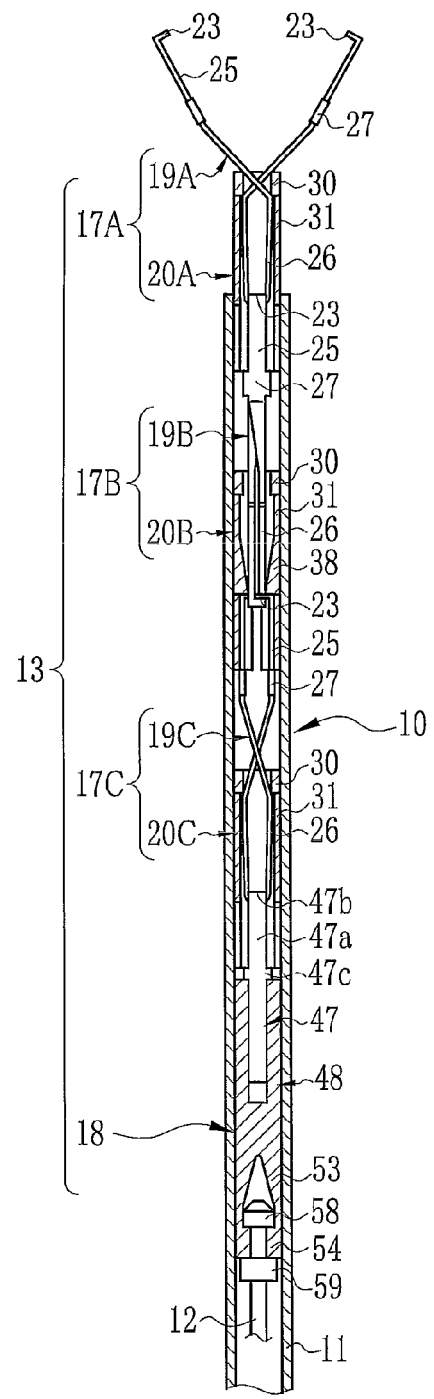

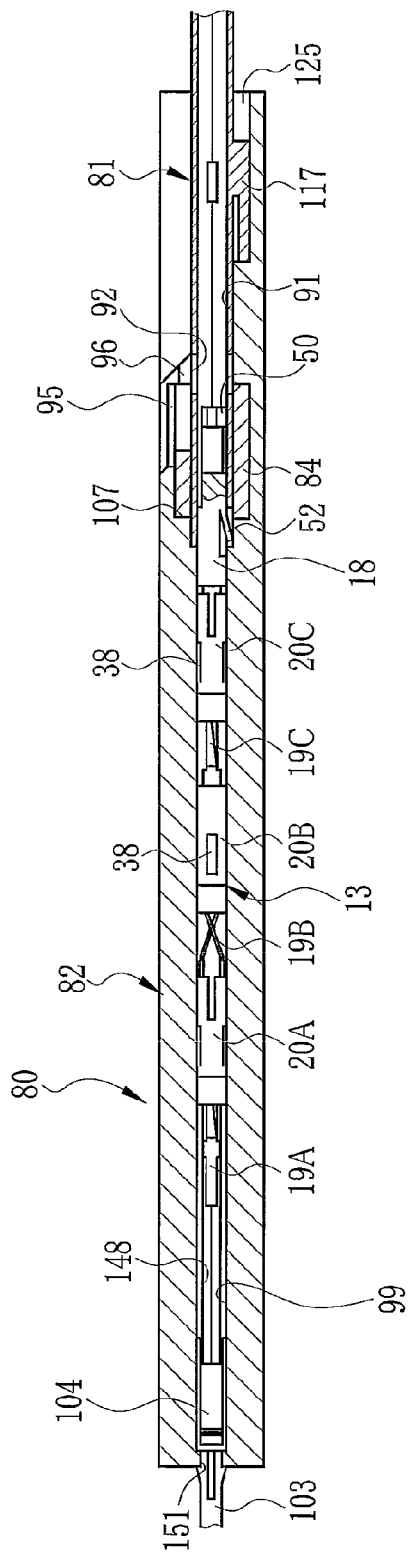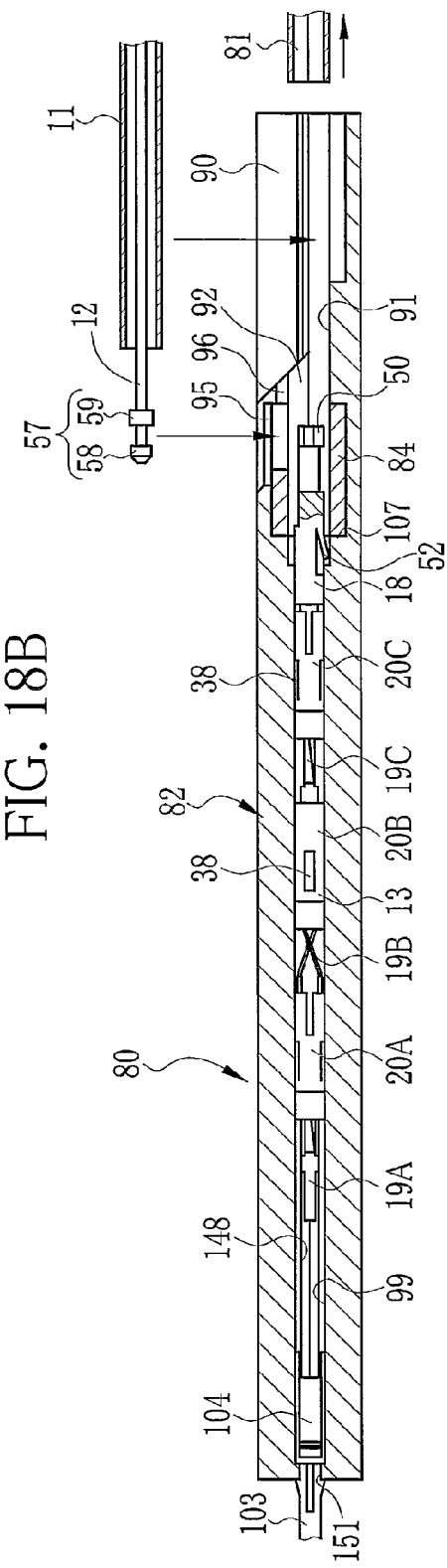

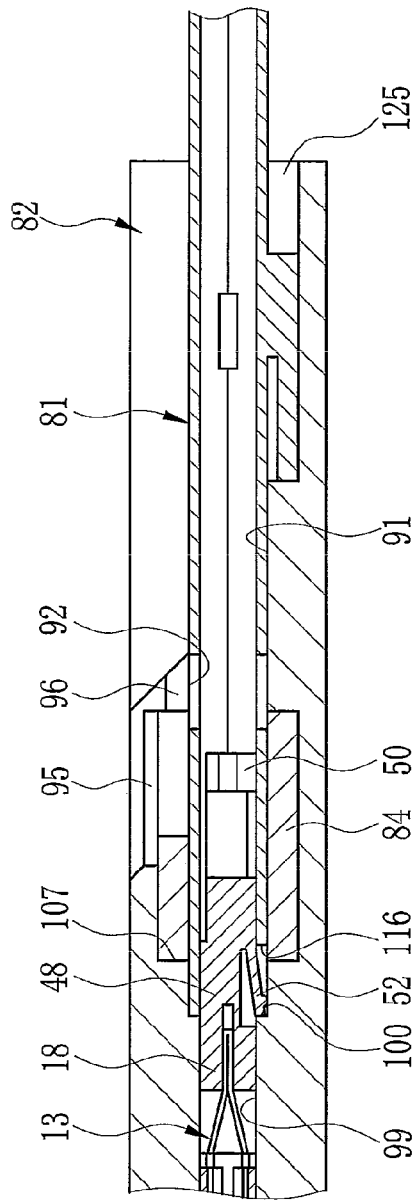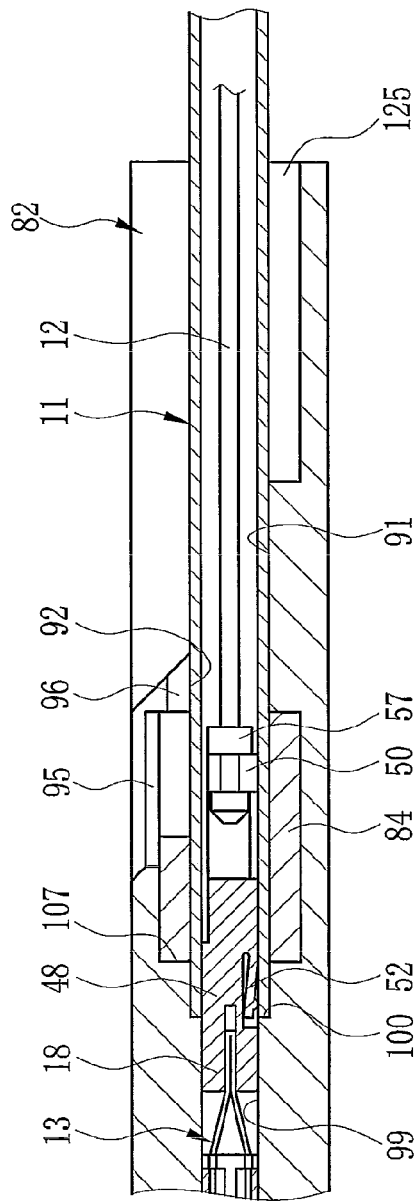

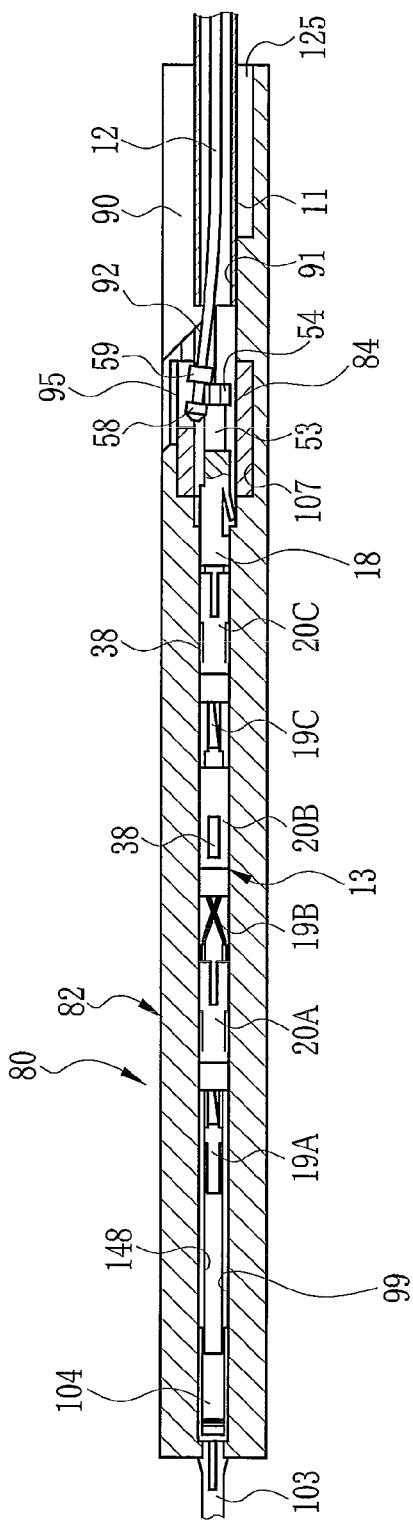
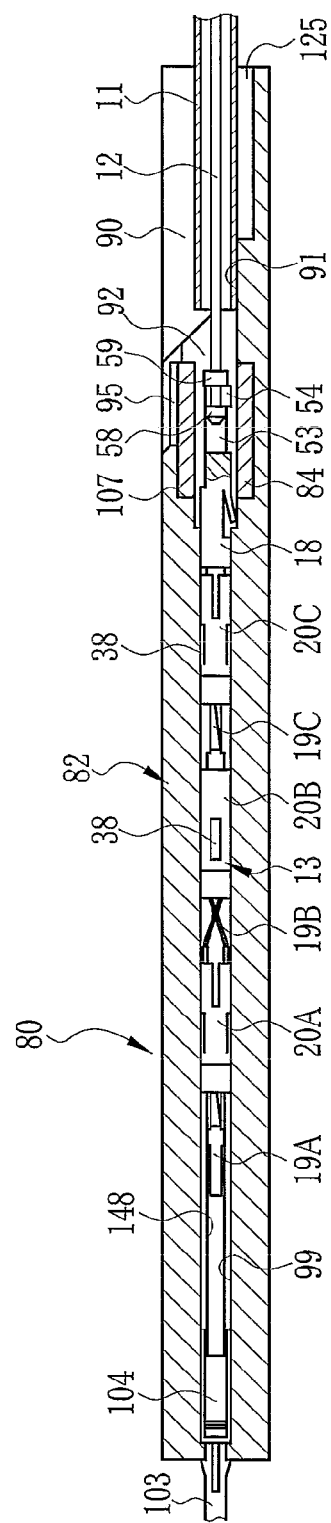
FIG. 20A
FIG. 20B

CLIP PACKAGE FOR CLIP APPLICATION APPARATUS

BACKGROUND OF THE INVENTION

1. Field of the Invention

The present invention relates to a clip package for a clip application apparatus. More particularly, the present invention relates to a clip package for a clip application apparatus, in which a clip assembly including a clip is used for the medical purpose of tissue clamping, and an operating wire can be fastened to a proximal end of the clip assembly easily and reliably.

2. Description Related to the Prior Art

Tissue clamping is known as medical treatment of a lesion in a gastrointestinal tract by use of an endoscope. In the clamping, a clip device of a small size is used to clamp the lesion for the purpose of hemostasis, suture and the like. A hemostatic clip application apparatus for the tissue clamping is entered in the body through a forceps channel of an endoscope, and clamps the tissue with the clip device at a distal end thereof. The hemostatic clip application apparatus includes a flexible sheath, an operating wire and a handle device. The flexible sheath of a cylindrical form is loaded with the clip device. The operating wire is fastened to a proximal end of the clip device within the flexible sheath. The handle device is manually operated for driving the flexible sheath and the operating wire.

U.S. Pat. No. 6,814,742 (corresponding to JP-A 2002-191609) discloses a method of loading the flexible sheath with a clip assembly by use of a housing which contains the clip assembly including the clip device and a fastening mechanism engaged with a proximal end of the clip device. In the loading method, a shaft head for hooking is disposed at a distal end of the operating wire protruding from a sheath end of the flexible sheath. The shaft head is inserted through an opening formed in the housing, set at a proximal end of the fastening mechanism, and pressed and fastened to the fastening mechanism by moving the operating wire in an axial direction. After the shaft head is fastened to the fastening mechanism, the operating wire is pulled to draw the clip assembly out of the housing for introduction in the flexible sheath. This is effective in loading of the clip assembly by simple operation of moving the operating wire back and forth in the axial direction.

The operating wire is shifted in the axial direction for pressing the shaft head into the fastening mechanism according to a known method of fastening the operating wire to the clip assembly. This requires suitable positioning of the fastening mechanism and the shaft head in relation to a radial direction. However, the operating wire has such a high flexibility that the shaft head at the distal end extends unstably. Operation of positioning of the shaft head and the fastening mechanism requires much labor. For example, if the position of the shaft head of the operating wire is different from the position of the fastening mechanism in the radial direction, no fastening is successfully carried out even by moving the shaft head toward the fastening mechanism. It is necessary to move back the operating wire and then to advance the operating wire for next positioning. If the shaft head is pressed on the fastening mechanism in offset positions in relation to the radial direction, failure in fastening is likely to occur due to an error in the engagement.

SUMMARY OF THE INVENTION

In view of the foregoing problems, an object of the present invention is to provide a clip package for a clip application apparatus, in which a clip assembly including a clip is used for the medical purpose of tissue clamping, and an operating wire can be fastened to a proximal end of the clip assembly easily and reliably.

In order to achieve the above and other objects and advantages of this invention, a clip package is provided, containing a clip device for use with a clip application apparatus and loading the clip application apparatus with the clip device. The clip package has a clip assembly, including the clip device, and a fastening mechanism, disposed at a proximal end of the clip device, for fastening to a shaft head of an operating wire inserted through a flexible sheath of the clip application apparatus. A coupling device includes a casing for containing the clip assembly in a manner movable from the fastening mechanism toward the flexible sheath, and a guide mechanism for pressing at least one of the fastening mechanism and the shaft head toward a remaining one thereof, for fastening thereof, the fastening mechanism emerging from the casing, the shaft head being overlapped on the fastening mechanism in an axial direction of the clip assembly.

The guide mechanism is slidable in a sliding direction transverse to the axial direction of the clip assembly, and includes a shifting wall for pressing the at least one of the shaft head and the fastening mechanism upon sliding, and the shifting wall is so inclined as to increase shift of the at least one of the shaft head and the fastening mechanism gradually upon sliding the guide mechanism.

The shifting wall includes a first inclined surface for initially contacting the at least one of the fastening mechanism and the shaft head upon sliding of the guide mechanism, and a second inclined surface for contacting the at least one of the fastening mechanism and the shaft head after contact of the first inclined surface, and an angle of an inclination of the first inclined surface is smaller than an angle of an inclination of the second inclined surface as viewed in the sliding direction of the guide mechanism.

The coupling device has a slide channel for receiving the guide mechanism in a slidable manner, and an inner surface of the slide channel supports the shifting wall.

The slide channel has a bias portion for biasing the shifting wall in a pressing direction while the shifting wall presses the at least one of the fastening mechanism and the shaft head upon sliding the guide mechanism.

The bias portion is a resiliently deformable spring plate, formed with an inner surface of the slide channel, and having a free end, and a projection is disposed to project from the free end, for contacting a peripheral surface of the guide mechanism to bias the shifting wall in the pressing direction.

The peripheral surface of the guide mechanism has a recess or opening for defining a distance from the projection to prevent interference when the guide mechanism is in an initial position prior to a start of sliding.

The guide mechanism includes a lower portion, opposed to the shifting wall in presence of the fastening mechanism and the shaft head, for supporting the fastening mechanism and the shaft head pressed by the shifting wall.

The guide mechanism includes a pushing portion for pushing a portion of the operating wire upon pressing of the shifting wall to the at least one of the fastening mechanism and the shaft head.

The pushing portion projects from the shifting wall in the pressing direction, and has a wedge form of which lateral sides are inclined to spread in the axial direction, the pushing portion enters the shaft head between plural shaft head portions thereof upon sliding the guide mechanism, to position the shaft head in the axial direction by contact of the lateral sides with the shaft head portions.

The coupling device is adapted to loading the flexible sheath with the clip assembly. The coupling device has a stage portion for connection of a housing for containing the clip assembly. The casing includes an insertion channel for receiving introduction of the clip assembly by advance of a distal end thereof from the housing shortly before loading in the flexible sheath.

The guide mechanism includes a receiving portion, engaged with the housing connected with the coupling device, for preventing removal of the guide mechanism from the coupling device.

The guide mechanism includes a guide portion, engaged with the fastening mechanism before pushing the at least one of the fastening mechanism and the shaft head, for positioning the fastening mechanism in the axial direction.

The guide portion is a guide surface so inclined as to increase a width thereof in the axial direction with reference to a backward direction of sliding.

The fastening mechanism has a rod shape, and has a contact surface, positioned erectly in a radial direction from a peripheral surface thereof, for engagement with the guide surface.

In another aspect of the invention, a clip package is provided, contains a clip device for use with a clip application apparatus and loads the clip application apparatus with the clip device. A clip assembly includes the clip device, and a fastening mechanism, disposed at a proximal end of the clip device, for fastening to a shaft head of an operating wire inserted through a flexible sheath of the clip application apparatus. A housing contains the clip assembly in a manner movable by advance of a distal end thereof. A coupling device includes a stage portion for connection of the housing, and an insertion channel for receiving introduction of the clip assembly by advance of the distal end from the housing, so as to load the flexible sheath with the clip assembly. A regulating claw is disposed to project from the clip assembly outwards and transversely to an axial direction thereof when the clip assembly is pulled from the housing. A regulating portion is disposed on the coupling device, for engagement with the regulating claw to regulate introduction of the fastening mechanism into the insertion channel.

The regulating portion has a regulating contact surface disposed near to an end opening of the insertion channel in a step shape.

The regulating claw projects when a distal end thereof resiliently deploys about a proximal end thereof secured to the fastening mechanism, and is engaged with the regulating portion.

The regulating claw is formed with the fastening mechanism by way of one piece.

Furthermore, a projection is disposed on an outer surface of the regulating claw, for reducing friction created on a surface contacting the regulating claw during movement of the clip assembly.

Furthermore, a guide mechanism presses at least one of the fastening mechanism and the shaft head toward a remaining one thereof, for fastening by applying pressure thereto, the shaft head being overlapped on the fastening mechanism in an axial direction of the clip assembly.

The fastening mechanism is positioned in a connecting position by engagement between the regulating claw and the regulating portion, for the guide mechanism to fasten the shaft head to the fastening mechanism.

Accordingly, the operating wire can be fastened to a proximal end of the clip assembly easily and reliably, because of the use of the guide mechanism operating in the coupling device.

BRIEF DESCRIPTION OF THE DRAWINGS

The above objects and advantages of the present invention will become more apparent from the following detailed description when read in connection with the accompanying drawings, in which:

FIG. 2A is a vertical section illustrating a sheath end of a flexible sheath of the multiple hemostatic clip application apparatus;

FIG. 2B is a vertical section illustrating the same as FIG. 2B but as viewed with a difference of 90 degrees;

FIG. 18A is a vertical section illustrating a state of introducing the multiple clip assembly from the housing into the coupling device;

FIG. 18B is a vertical section illustrating a state of removing the housing from the coupling device after the state of FIG. 18A;

FIGS. 19A and 19B are vertical sections illustrating states of a regulating claw in the course of introducing the multiple clip assembly into the coupling device and loading of a flexible sheath;

FIG. 20A is a vertical section illustrating a state of fastening the operating wire to the multiple clip assembly after inserting a flexible sheath in the coupling device;

FIG. 20B is a vertical section illustrating a finally fastened state the operating wire to the multiple clip assembly;

DETAILED DESCRIPTION OF THE PREFERRED EMBODIMENT(S) OF THE PRESENT INVENTION

Figure 1:
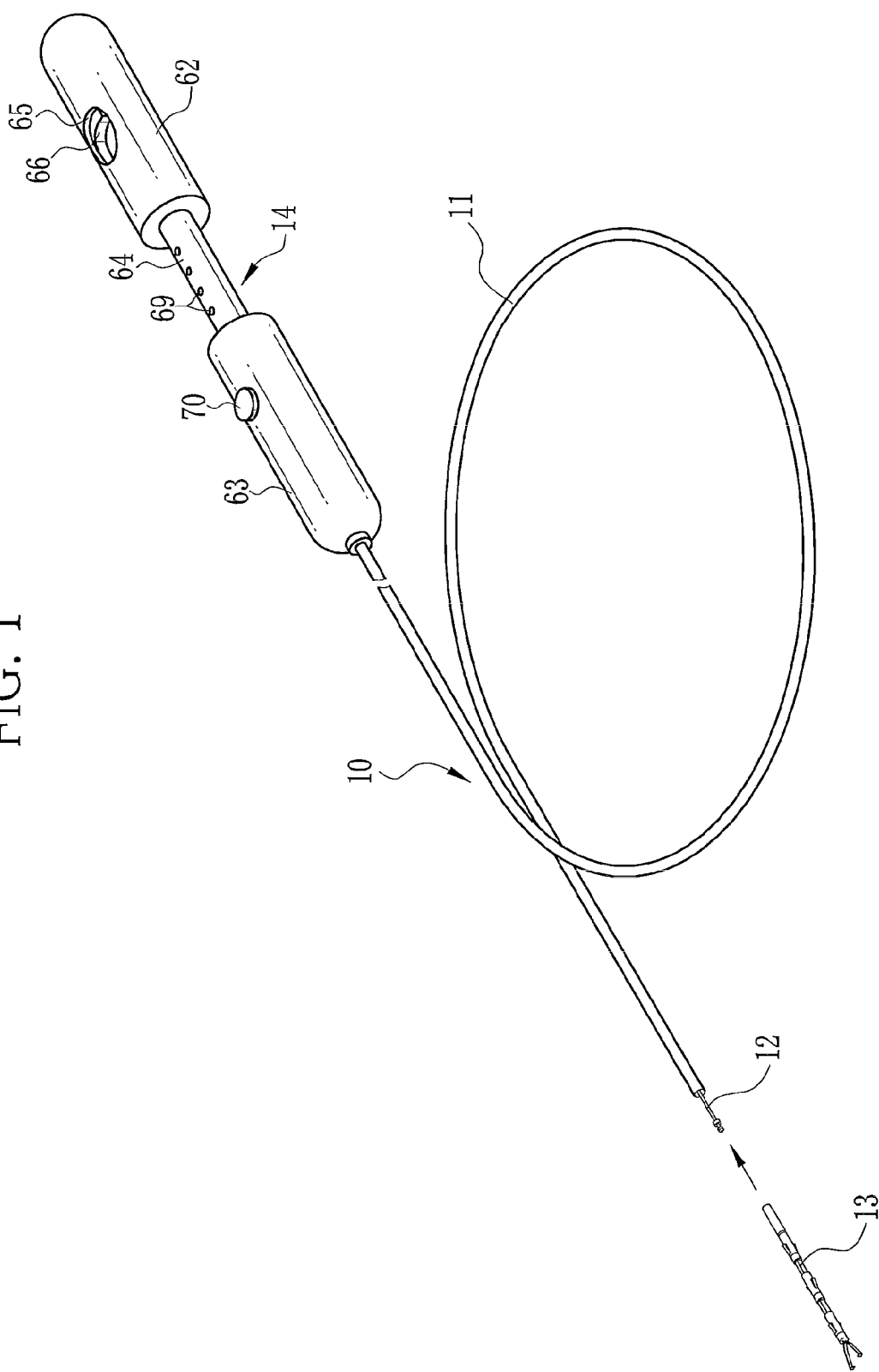
FIG. 1 is a perspective view illustrating a multiple hemostatic clip application apparatus.

In FIG. 1, a multiple hemostatic clip application apparatus 10 of the invention is illustrated. The multiple hemostatic clip application apparatus 10 includes a cylindrical flexible sheath 11, an operating wire 12, a multiple clip assembly 13 or clip train, and a handle device 14.

The flexible sheath 11 has a great length. The operating wire 12 is inserted through the flexible sheath 11 movably back and forth. The multiple clip assembly 13 includes a train of plural clips fastened to one another. The multiple clip assembly 13 is contained in a portion of a sheath end of the flexible sheath 11. A proximal end of the multiple clip assembly 13 is fastened to a distal end of the operating wire 12. The handle device 14 is connected with proximal ends of the flexible sheath 11 and the operating wire 12, and is pulled manually. When the flexible sheath 11 is pulled, each of the clips in the multiple clip assembly 13 is pushed forwards through the sheath end. The clip is open when pushed out of the flexible sheath 11, and is closed when the operating wire 12 is pulled.

In FIG. 2A, the sheath end of the flexible sheath 11 loaded with the multiple clip assembly 13 is depicted for a state shortly before tissue clamping of a first one of the clip devices. In FIG. 2B, the sheath end is viewed with a difference of 90 degrees from FIG. 2A.

The multiple clip assembly 13 includes a train of hemostatic clip devices 17 and a fastening clip device 18. The clip devices 17A, 17B and 17C (in place of the numeral 17) are fastened to one another serially. The fastening clip device 18 is fastened to the clip device 17C which is one of the clip devices 17 disposed on the proximal side. The clip devices 17 include clips 19 and tubular shells 20 or retaining rings. The tubular shells 20A, 20B and 20C (in place of the numeral 20) are disposed around respectively the clips 19A, 19B and 19C (in place of the numeral 19). Among the clips 19, a proximal end of a first one of the clips 19 is fastened to a second one of the clips 19 so as to fasten the clip devices 17 in the train.

Figure 3:
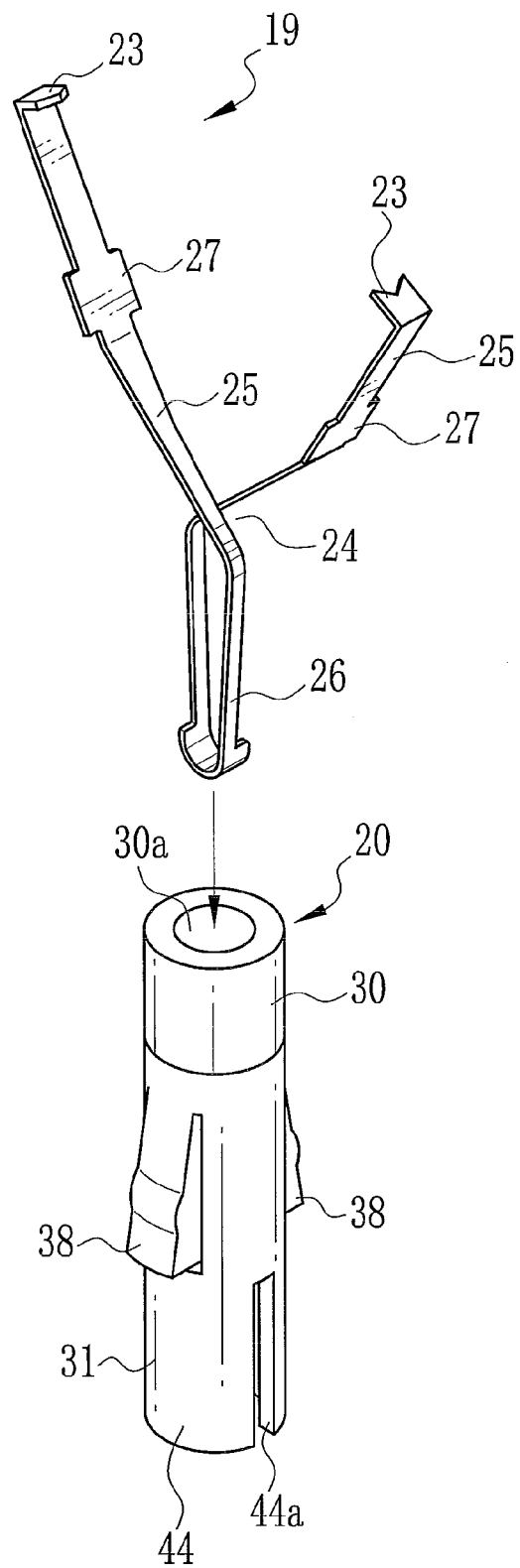
FIG. 3 is a perspective view illustrating a clip device and a tubular shell.

In FIG. 3, two claws 23 are formed with each of the clips 19. At first, an elongate strip of a single plate is bent at an angle of 180 degrees. Segment portions extending at ends of the strip are intersected with one another, and opposed to one another by curving, to define the claws 23. The clip 19 includes a crossed portion 24, arms 25 and a turn 26. The crossed portion 24 is defined by crossing the strip. The arms 25 are located at the free ends. The turn 26 is constituted by the closed end. Side projections 27 are formed on edges of the arms 25, are positioned at an intermediate point, and partially define portions with a greater width.

When the arms 25 of the clip 19 are free without receiving external force, the claws 23 are open and away from one another. The claws 23 become meshed with one another and are in a closed position for tissue clamping when the arms 25 are deformed toward one another. The claws 23 are a V-shaped projection and a notch in the combination for the purpose of clamping body tissue. An example of material for the clip 19 is metal with biocompatibility, for example stainless steel SUS 631 for springs.

Each of the tubular shells 20 includes a push sleeve 30 and a support sleeve 31. The push sleeve 30 of metal is positioned at the distal end. The support sleeve 31 of a plastic material is positioned at a proximal end of the push sleeve 30. A narrow bore 30a is formed inside the push sleeve 30. The clip device 17 is constructed by inserting each of the clips 19 with the turn 26 and by disposing one of the tubular shells 20 about the clip 19. The push sleeve 30 is set in an initial position to cover the crossed portion 24. The arms 25 of the clip 19 are in an open state.

The push sleeve 30 with the narrow bore 30a pushes the arms 25 when the clip 19 is drawn in the tubular shell 20, to clamp and close the claws 23. The claws 23 exert force of clamping when the arms 25 are pushed toward one another. A diameter of the narrow bore 30a is smaller than a width of the side projections 27 of the clip 19, so that a portion of the clip 19 in front of the side projections 27 will not be inserted in the tubular shell 20.

Figure 4:
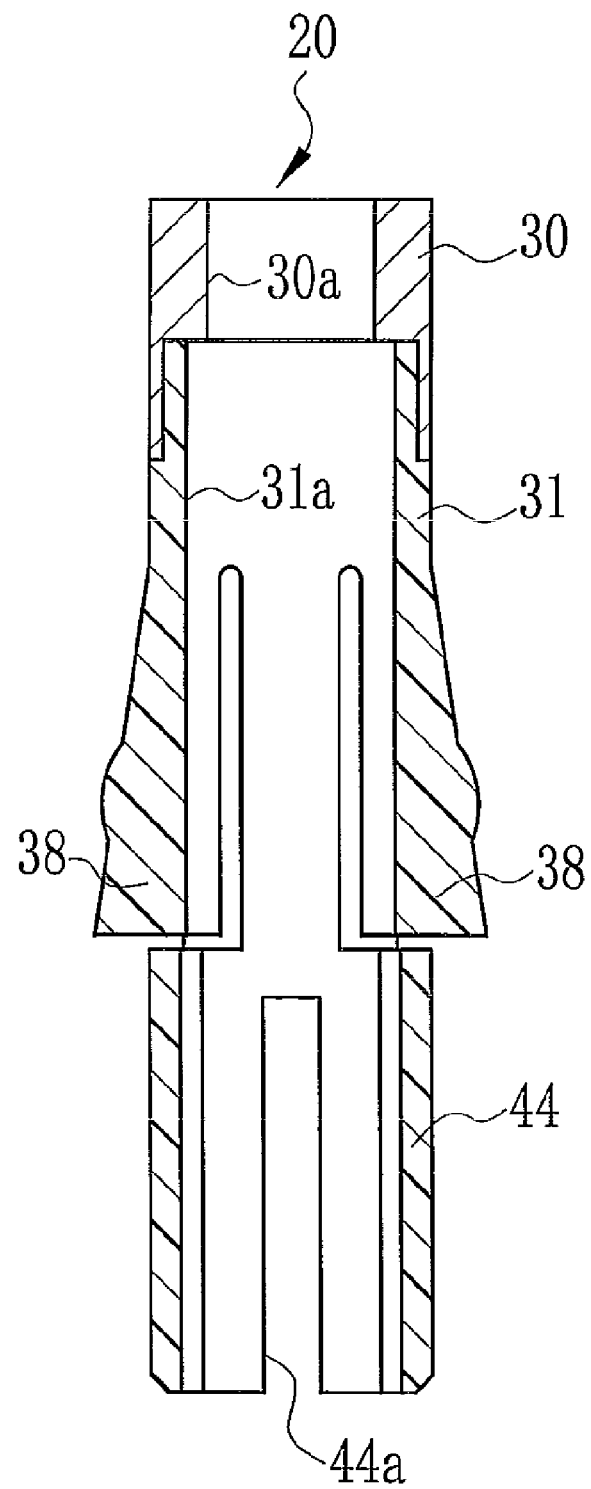
FIG. 4 is a vertical section illustrating the tubular shell.

In FIG. 4, a bore 31a is formed in the support sleeve 31 and extends from the narrow bore 30a. The turn 26 inserted in the narrow bore 30a is contained in the bore 31a. Two fins 38 or skirt portions are formed on a peripheral surface of the support sleeve 31 and positioned symmetrically with reference to its axis. The fins 38 extend with an increasing diameter in a direction from the distal end toward the proximal end of the support sleeve 31, and when free without receiving external force, are deployed with their resiliency, and when depressed, become stowed by entry in the support sleeve 31.

The tubular shell 20 is disposed about the clip 19 to set an opening direction of the claws 23 with a difference of 90 degrees from a deploying direction of the fins 38. The fins 38 come to clamp the turn 26 contained in the bore 31a when the multiple clip assembly 13 is closed inside the flexible sheath 11, so that the tubular shell 20 is combined with the clip 19.

The clip devices 17 of a plural number are fastened serially to one another by engaging the claws 23 of a rear one of the clips 19 with the turn 26 of the clips 19. The tubular shell 20 covers the claws 23 of a rear one of the clips 19, and maintains the fastened state between the clips 19 by keeping the claws 23 closed. The side projections 27 of the clips 19 have a greater width than a diameter of the bore 31a, and contact a proximal end of the tubular shell 20 when disposed behind the tubular shell 20. Thus, the tubular shell 20 is prevented from moving from the initial position toward the proximal side of the multiple clip assembly 13.

The tubular shell 20 has a proximal end region 44 disposed to extend further than the fins 38. Two end channels 44a are formed in the proximal end region 44, and disposed with a difference from the fins 38 with an angle of 90 degrees. Each of the end channels 44a extends in the axial direction of the tubular shell 20, for the proximal end region 44 to be deformable resiliently to enlarge its inner diameter. The end channels 44a make the tubular shell 20 flexible, so as to flex the multiple clip assembly 13 in compliance with flexing of the endoscope. As an inner diameter of the proximal end region 44 is enlarged because of the end channels 44a, engagement of two of the clips 19 within the tubular shell 20 is facilitated in the course of assembly.

Note that the support sleeve 31 is formed from a material which has biocompatibility and has sufficient resiliency and rigidity for the performance of the fins 38. A preferable example of the material for the support sleeve 31 is polyphenylsulfone (PPSU or PPS).

Figure 5:
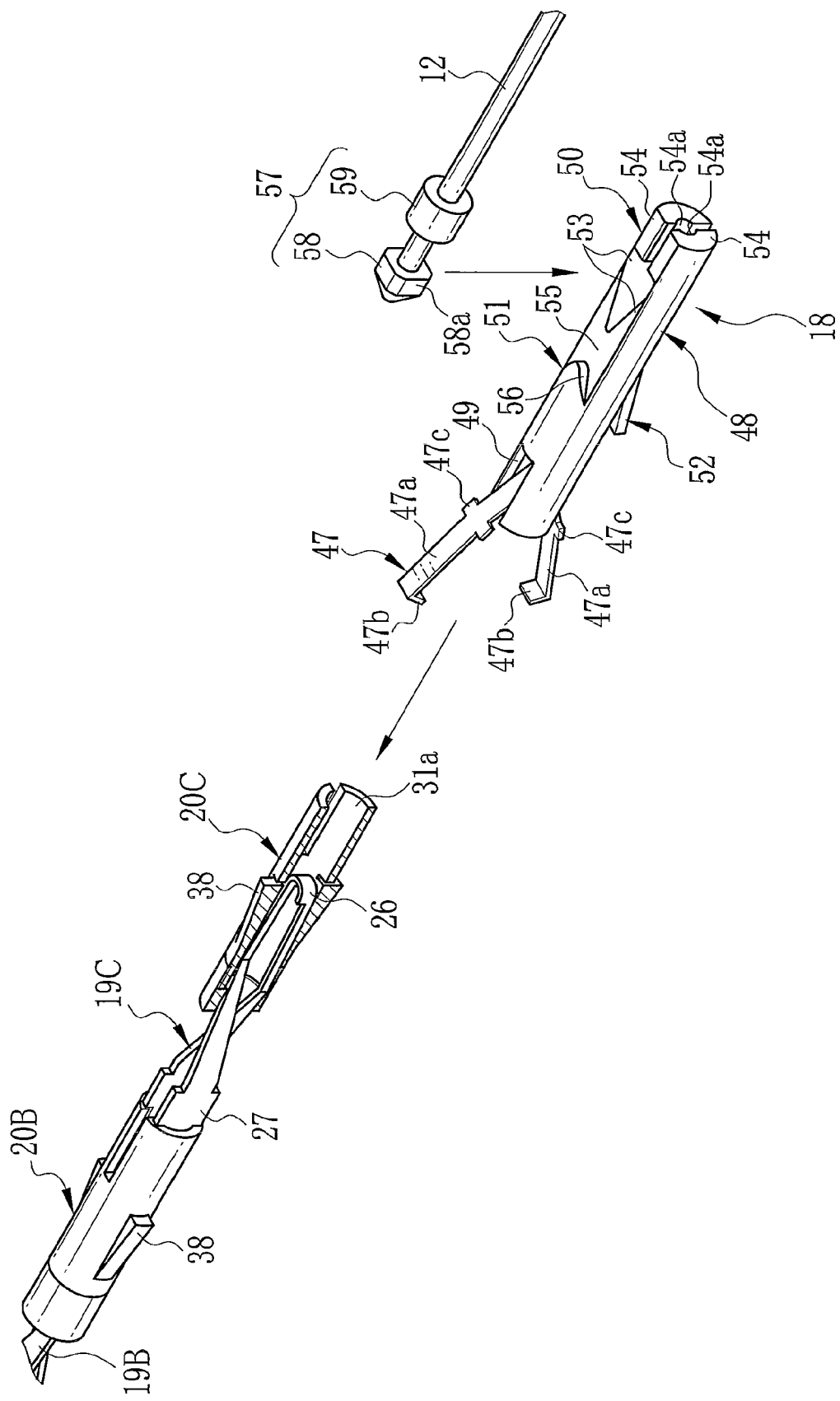
FIG. 5 is an exploded perspective view illustrating a fastened state of a rear one of the clip devices, a fastening clip device, and an operating wire.

In FIG. 5, the fastening clip device 18 includes a fastening clip 47 or dummy clip and a support 48. The fastening clip 47 is engaged with the turn 26 of the clip 19C. A pair of arms 47a of the fastening clip 47 are defined by bending a single elongate strip of a metal plate. The arms 47a are in an open state if free without external force. Jaws 47b are formed with ends of the arms 47a. Side projections 47c are formed with intermediate portions of the arms 47a. The fastening clip 47 may be produced from a material the same as that for the clips 19.

The fastening clip 47 becomes inserted in the bore 31a of the tubular shell 20C by rotationally changing the direction of the arms 47a with a difference of 90 degrees from the direction of opening and closing of the clip 19C on the proximal side. The jaws 47b of the fastening clip 47 are engaged with the turn 26 of the clip 19C. The tubular shell 20C is kept in connection as the jaws 47b are kept from moving to the open position.

Figure 6:
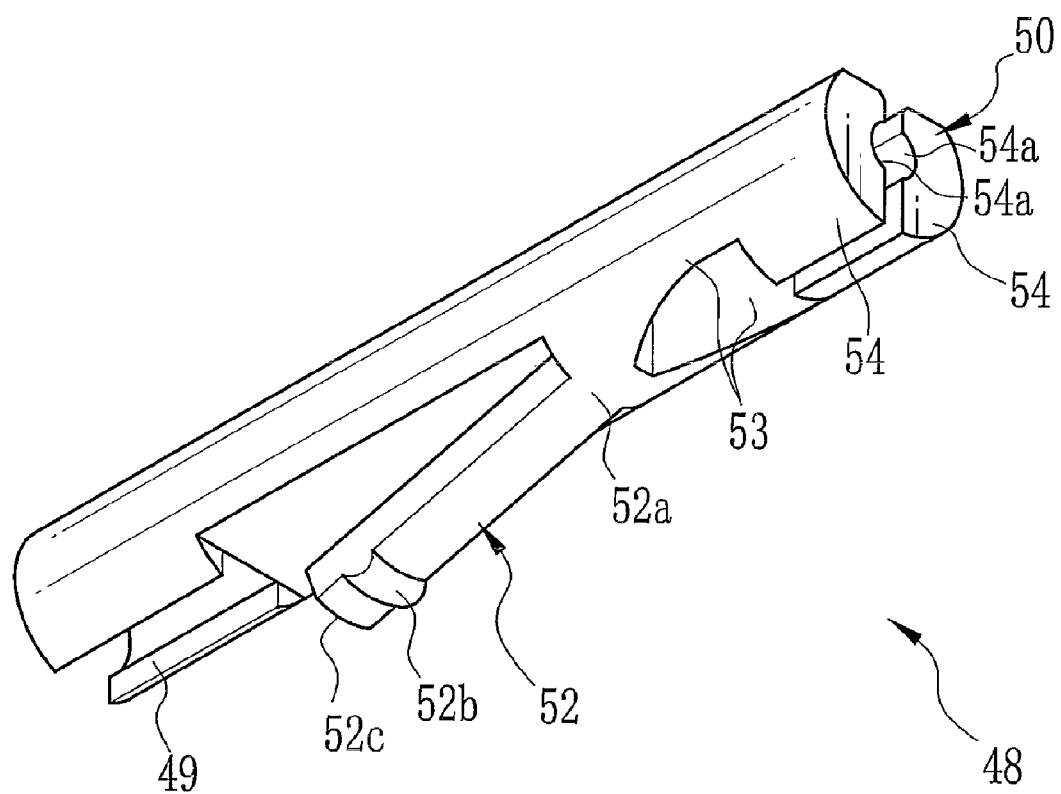
FIG. 6 is a bottom perspective view illustrating a support for a fastening clip.

In FIGS. 5 and 6, the support 48 is a rod-shaped part formed from the same material as the support sleeve 31 in the tubular shell 20. A support recess 49 is formed in a distal end of the support 48 for retaining the fastening clip 47. A fastening mechanism 50 is disposed at a proximal end of the support 48 for fastening to the operating wire 12.

The fastening mechanism 50 includes a pair of cavity walls 53 with resiliency, and a pair of clamping walls 54. The cavity walls 53 are resilient in the radial direction of the support 48. The clamping walls 54 are located at the end of the cavity walls 53. An interval between the clamping walls 54 is smaller than an outer diameter of the operating wire 12. Also, grooves 54a of an arcuate shape as viewed in section are formed inside the clamping walls 54, extend along the axis of the support 48, and have a diameter equal to that of the operating wire 12.

The support 48 includes a positioning wall 51 and a regulating claw 52. The positioning wall 51 positions the support 48 axially at the time of fastening to the operating wire 12 by use of a multiple clip package 80 or multiple clip holder, which will be described later with FIG. 8. The regulating claw 52 prevents the support 48 from excessive introduction into a coupling device 82 in the advance of the multiple clip assembly 13 from a housing 81 or barrel of the multiple clip package 80 into the coupling device 82. The positioning wall 51 and the regulating claw 52 are disposed between the support recess 49 and the fastening mechanism 50.

The positioning wall 51 includes a flat surface 55 and a contact surface 56. The flat surface 55 is positioned on an upper side from the cavity walls 53, and defined by chamfering a rod surface of the support 48. The contact surface 56 is defined between the rod surface and the flat surface 55, and erect crosswise to the axial direction. The contact surface 56 is in a triangular shape of a projection which protrudes from a distal end to a proximal end of the support 48. In consideration of a guide slider 84 to be described later (see FIG. 8), the flat surface 55 is positioned in such a manner that the guide slider 84 is movable safely without being blocked. The contact surface 56 is so positioned as to contact a guide surface 170 of the guide slider 84 (see FIG. 14).

The regulating claw 52 includes a proximal end 52a and a distal end 52c. The proximal end 52a is a base point of extension from the support 48. The distal end 52c protrudes outwards from a rod surface of the support 48. The regulating claw 52 has a width increasing in a direction toward the distal end of the support 48. The regulating claw 52, when in a free state without external force, is open to protrude the distal end 52c outwards by turning about the proximal end 52a. The regulating claw 52, when depressed by external force, becomes closed and stowed in the support 48.

The regulating claw 52 has a width greater than that of the fins 38 of the tubular shell 20. This is for the purpose of preventing the regulating claw 52 from entering each one of fin receiving slots 114 of FIG. 11 for receiving the fins 38 in operation of loading the flexible sheath 11 with the multiple clip assembly 13 by use of the multiple clip package 80 of FIG. 8.

A projection 52b is formed on the distal end 52c of the regulating claw 52 to project outwards. The projection 52b contacts an inner surface of the housing 81 of the multiple clip package 80 of FIG. 11, and prevents interference of the distal end 52c of the regulating claw 52 with the fin receiving slots 114. Also, the projection 52b is effective in reducing resistance with friction by contacting the inner surface of the flexible sheath 11 containing the support 48.

An example of the flexible sheath 11 in FIG. 1 is a flexible coil sheath in which a wire of metal is tightly wound in a coiled form. An inner diameter of the flexible sheath 11 is so determined that the turn 26 of a first one of the clips 19 is disengaged from the claws 23 of a second one of the clips 19. The inner diameter of the flexible sheath 11 is greater than a sum of a length of the claws 23 and a width of an engaged portion of the turn 26 with the claws 23.

The operating wire 12 is a wire of metal having biocompatibility. In FIG. 5, a shaft head 57 for hooking is disposed at the wire end of the operating wire 12 for connection with the fastening clip device 18. The shaft head 57 includes a front shaft head portion 58 and a rear shaft head portion 59 arranged on the operating wire 12.

The front shaft head portion 58 includes a lateral surface 58a on a quadrilateral prismatic part, and an inclined surface 58b on a quadrilateral pyramidal part. The lateral surface 58a has one side line which has a length equal to the size of the clearance between the cavity walls 53. The inclined surface 58b has a size corresponding to the clearance between the cavity walls 53. The rear shaft head portion 59 has a cylindrical shape having a diameter which is greater than the outer diameter of the front shaft head portion 58 and slightly smaller than an outer diameter of the support 48. The rear shaft head portion 59 is distant from a proximal end of the front shaft head portion 58 by a distance which is equal to the length of the clamping walls 54 in the axial direction.

The front shaft head portion 58 is inserted between the cavity walls 53 by moving downwards, and contacts the clamping walls 54 at the end of the cavity walls 53. A portion of the operating wire 12 between the shaft head portions 58 and 59 is clamped by the clamping walls 54. The rear shaft head portion 59 contacts a proximal end of the clamping walls 54. This is effective in transmitting the pull and rotation of the operating wire 12 to the multiple clip assembly 13, and prevents the multiple clip assembly 13 from moving together with the flexible sheath 11 even with friction created by pulling the flexible sheath 11.

In FIG. 1, the handle device 14 includes a wire handle 62 and a sheath handle 63. The wire handle 62 is cylindrical. An elongated pipe 64 is disposed at a distal end of the wire handle 62, and has a smaller diameter than the wire handle 62. An opening 65 is formed in the middle of the wire handle 62. There is a pull arm 66 of which a rear portion appears partially through the wire handle 62. An operator inserts his or her finger to pull the pull arm 66. A proximal end of the operating wire 12 is retained on the pull arm 66, the operating wire 12 extending through the sheath handle 63, the elongated pipe 64 and the wire handle 62 by insertion.

The pull arm 66 is kept movable back and forth in the wire handle 62, namely in an axial direction of the wire handle 62. The pull arm 66, when in a home position, appears in the opening 65, and when in a pull position, is slid in the axial direction. A length of slide of the pull arm 66 is determined to correspond to a length of pull of the operating wire 12 within the flexible sheath 11 for closing the clips 19 protruding from the sheath end of the flexible sheath 11. A spring (not shown) biases the pull arm 66 toward the home position. The spring compresses when the pull arm 66 is pulled back, but pushes the pull arm 66 forwards when the pull arm 66 is released from the finger.

The sheath handle 63 has a cylindrical shape and has an opening at its proximal end. A proximal end of the flexible sheath 11 is attached to a distal end of the sheath handle 63. When the sheath handle 63 is pulled back toward the wire handle 62, the flexible sheath 11 is pulled. The sheath handle 63 is mounted around the elongated pipe 64 in a manner slidable in the axial direction of pulling the flexible sheath 11.

A lock mechanism is disposed in the sheath handle 63. Notches 69 are formed in an upper portion of the elongated pipe 64, and adapted to locking the sheath handle 63 in one of plural positions of slide. A release button 70 is disposed on an upper portion of the sheath handle 63, and operable for releasing the lock mechanism for sliding. An interval between the notches 69 corresponds to a length of moving the flexible sheath 11 for each time of advancing one of the clip devices 17 from the flexible sheath 11. The number of the notches 69 corresponds to the number of the clip devices 17 insertable in the flexible sheath 11.

Figure 7A:
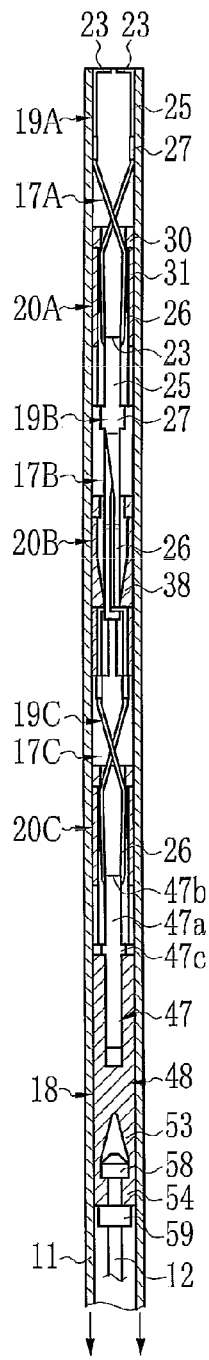
FIG. 7A is a section illustrating a first step in a sequence of tissue clamping with the multiple hemostatic clip application apparatus.

The operation of the multiple hemostatic clip application apparatus 10 is described now. In FIG. 7A, the flexible sheath 11 is loaded with the multiple clip assembly 13 in which a distal end of the first clip 19A is flush with a sheath end of the flexible sheath 11. The flexible sheath 11 is inserted in a forceps channel of the endoscope entered in a body cavity. The sheath end of the flexible sheath 11 protrudes from the forceps opening of the endoscope, and accesses a lesion or body tissue.

Figure 7B:
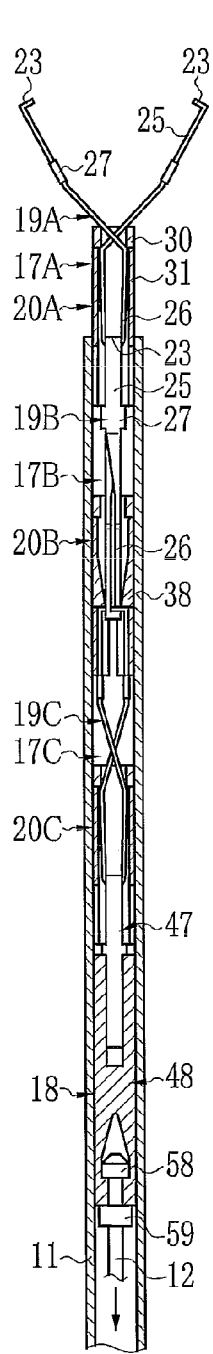
FIG. 7B is a section illustrating a step of opening the clip device in the clamping sequence.

When the sheath handle 63 is pulled at a predetermined distance, then the flexible sheath 11 comes back at the predetermined distance relative to the operating wire 12. The multiple clip assembly 13 advances relative to the flexible sheath 11 because of fastening between the operating wire 12 and the multiple clip assembly 13. In FIG. 7B, the first clip device 17A is advanced through the sheath end of the flexible sheath 11.

When the flexible sheath 11 is pulled, force of friction to the proximal side is exerted between the flexible sheath 11 and the tubular shells 20A-20C inside. However, the tubular shells 20A-20C are kept in association with the clips 19A-19C by the fins 38 in the stowed state, and are prevented from moving to the proximal side by the side projections 27 of the clips 19B and 19C and the side projections 47c of the fastening clip 47. Thus, the tubular shells 20A-20C shift together with the clips 19A-19C forwards relative to the flexible sheath 11 without shifting backwards with the flexible sheath 11.

In the first clip 19A advanced through the sheath end of the flexible sheath 11, the claws 23 become open with their resiliency. In FIG. 2A, the fins 38 of the tubular shell 20A become deployed with a width greater than an inner diameter of the flexible sheath 11, and are engaged with the sheath end of the flexible sheath 11 without return into the flexible sheath 11.

The multiple hemostatic clip application apparatus 10 is moved to press the claws 23 of the clip 19A against the body tissue in the open state. Then the pull arm 66 of the wire handle 62 is manually pulled to pull the operating wire 12 at a predetermined amount. The clips 19A-19C are pulled equally in a state engaged with one another serially from the fastening clip device 18.

Figure 7C:
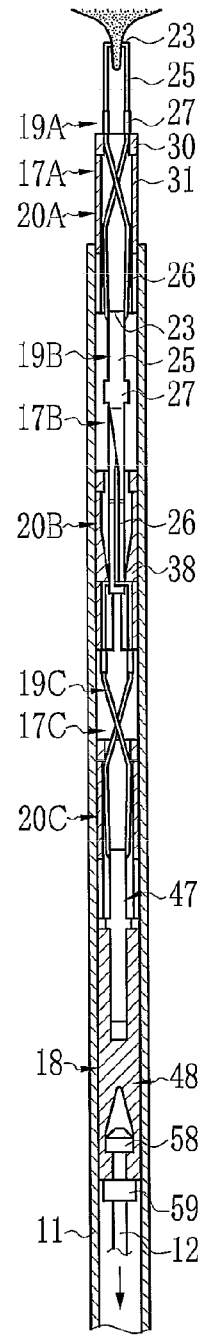
FIG. 7C is a section illustrating tissue clamping in the clamping sequence.

In the state of FIG. 7C, the fins 38 of the tubular shell 20A protruding from the flexible sheath 11 are deployed. The clip 19A is free from retention with the fins 38. The tubular shell 20A is prevented from returning into the flexible sheath 11 by the fins 38, which are kept deployed by the sheath end. In FIG. 7C, the first clip 19A is moved back relative to the tubular shell 20A by the pull of the operating wire 12. Thus, the push sleeve 30 is positioned directly under the side projections 27 of the clip 19A, finally to close the clip 19A by the tubular shell 20A.

Figure 7D:
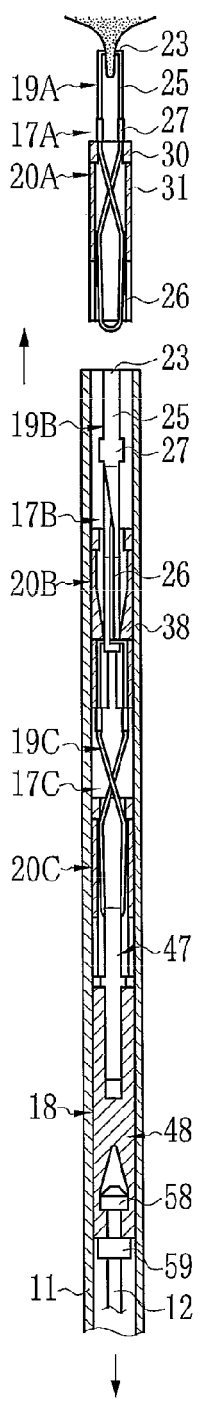
FIG. 7D is a section illustrating a step of separating the clip device from second and other clip devices.

At the same time as the clip 19A is closed fully, the engaged portion between the clips 19A and 19B comes away from the proximal end of the tubular shell 20A. The arms 25 of the clip 19B are open with their resiliency to contact the inside of the flexible sheath 11. An interval between the claws 23 becomes greater than the width of the turn 26 of the clip 19A to disengage the clip 19A from the clip 19B. In FIG. 7D, the sheath end of the flexible sheath 11 is released from the tissue or lesion of the body part, to separate the clip device 17A from the sheath end.

The pull arm 66 is returned by the bias of the spring (not shown) to the home position upon termination of its pull. Thus, the operating wire 12 moves toward the distal end inside the flexible sheath 11 to push the fastening clip device 18 and the clips 19B and 19C. A distal end of the clip 19B becomes flush again with the sheath end of the flexible sheath 11 as illustrated in FIG. 7D. In a manner similar to the first clip device 17A, the clip devices 17B and 17C are operated for tissue clamping by manual handling of the handle device 14.

Figure 8:
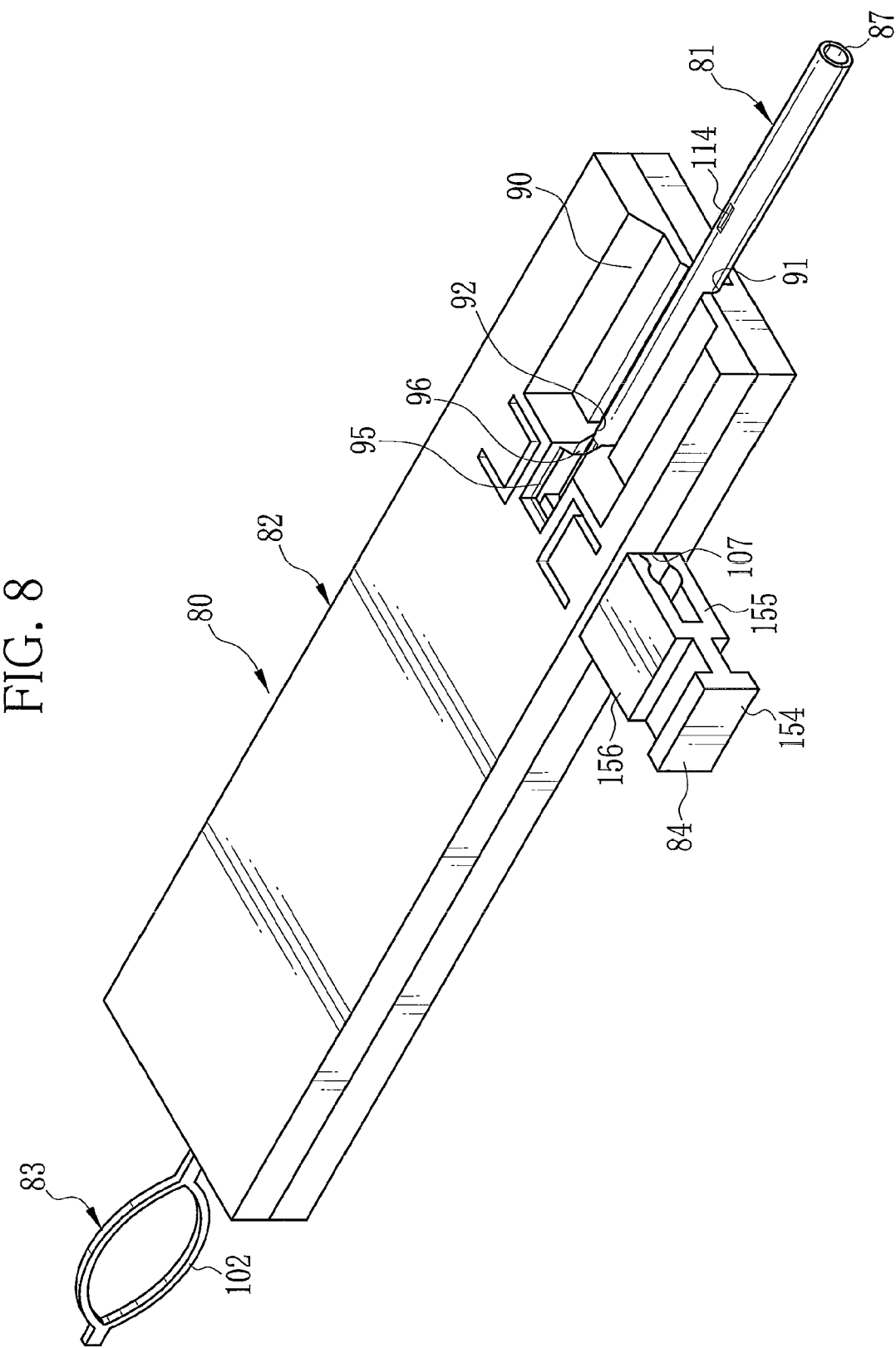
FIG. 8 is a perspective view illustrating a multiple clip package.
Figure 9:
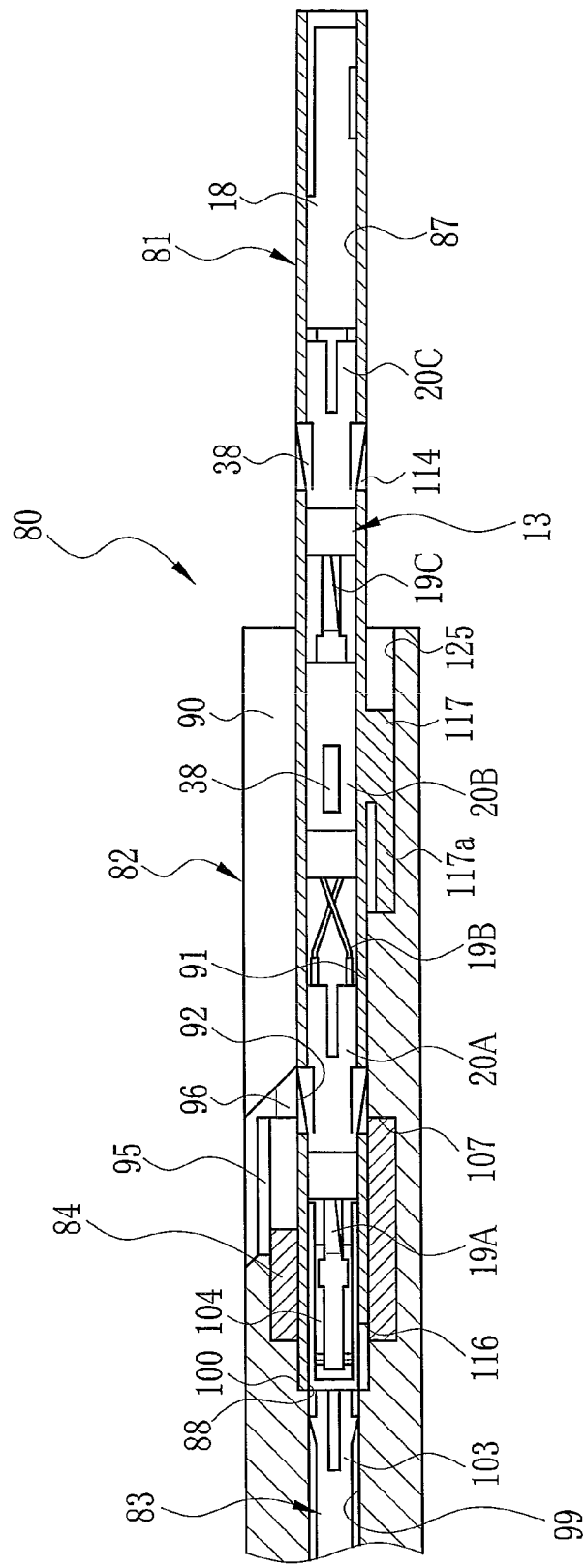
FIG. 9 is a vertical section illustrating the multiple clip package.
Figure 10:
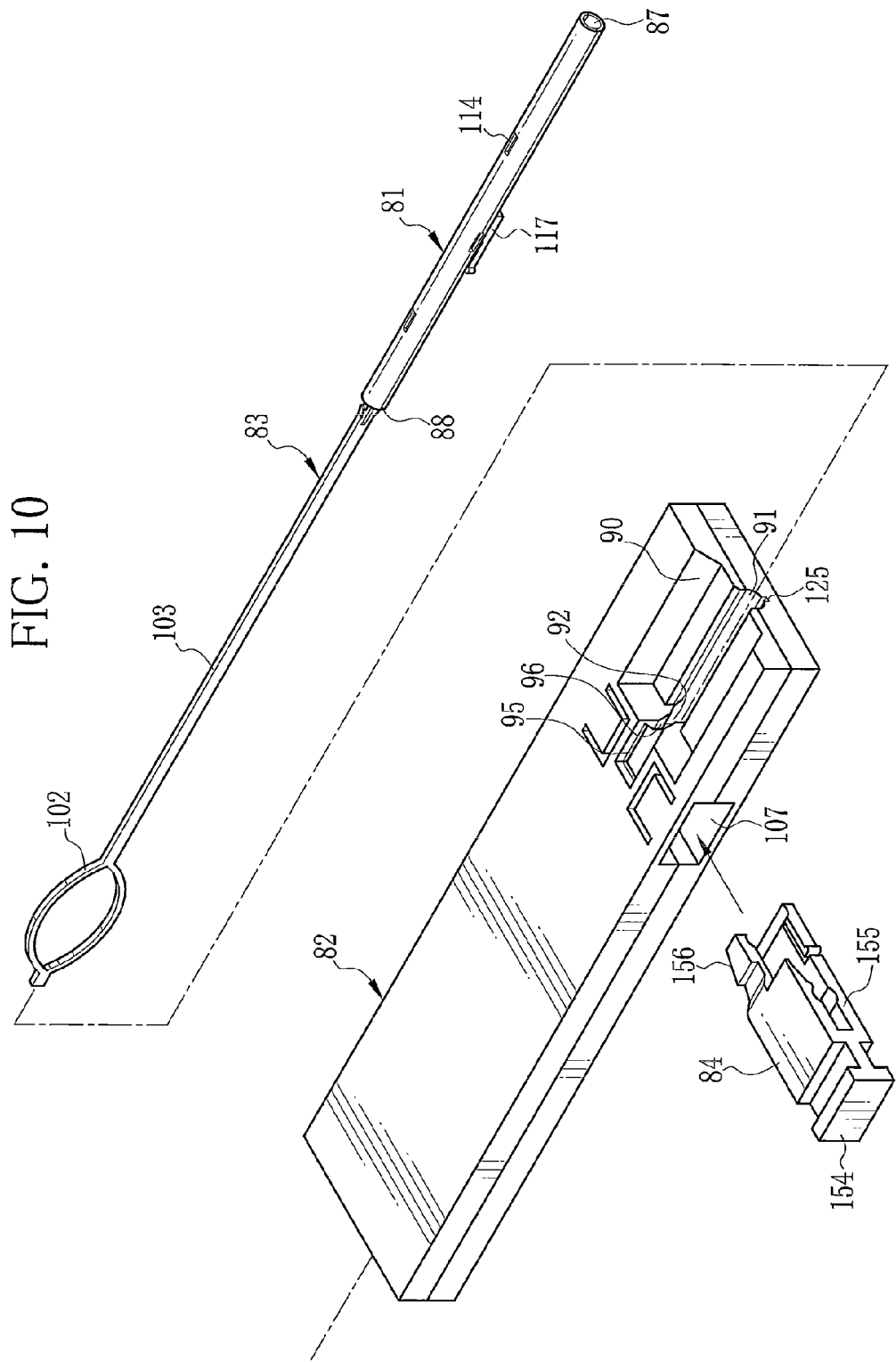
FIG. 10 is a perspective view illustrating the multiple clip package.

The multiple clip package 80 of the invention is described now. In FIGS. 8-10, the multiple clip package 80 includes the housing 81, the coupling device 82, the guide slider 84 and also a pull rod structure 83. With the coupling device 82, an end of the housing 81 is connected. The pull rod structure 83 is assembled with the coupling device 82. The housing 81 contains the multiple clip assembly 13. The coupling device 82 introduces the multiple clip assembly 13 from the housing 81 by use of the pull rod structure 83, and loads the multiple clip assembly 13 in the flexible sheath 11 after closing the fins 38. The guide slider 84 is a guide mechanism operable for fastening the operating wire 12 to the fastening clip device 18.

A barrel cavity 87 is defined in the housing 81. An outer diameter of the housing 81 is substantially equal to an outer diameter of the flexible sheath 11. A diameter of the barrel cavity 87 is substantially equal to the inner diameter of the flexible sheath 11. The multiple clip assembly 13 is contained in the barrel cavity 87. An exit opening 88 is open at a distal end of the housing 81. The clip 19A in the multiple clip assembly 13 is disposed close to the exit opening 88 on the distal side of the housing 81. In the support 48, the regulating claw 52 is in the depressed state while the multiple clip assembly 13 is contained in the housing 81.

Figure 11:
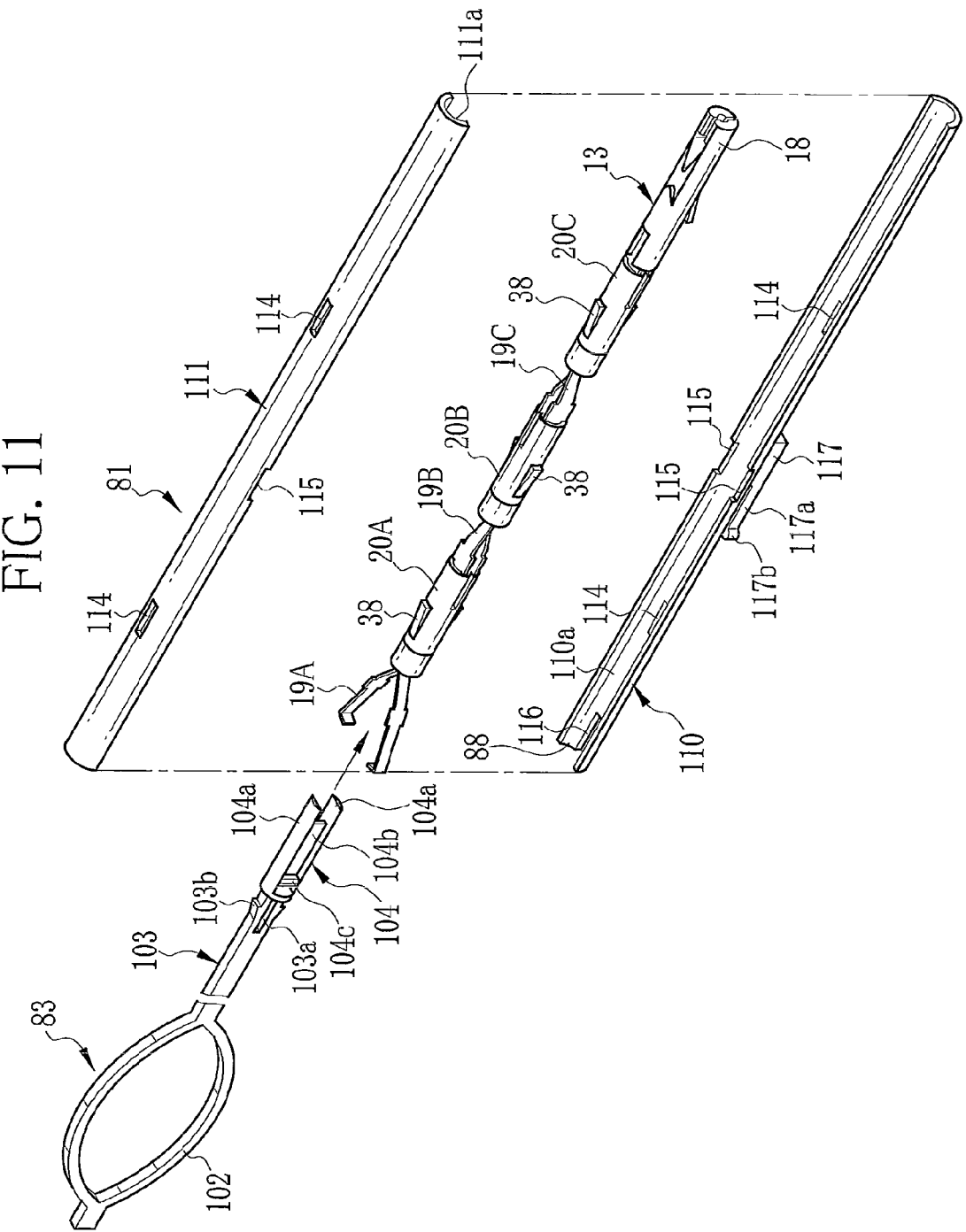
FIG. 11 is a perspective view illustrating a multiple clip assembly and a pull rod structure with a housing.

In FIG. 11, the housing 81 is constituted by a lower housing half 110 and an upper housing half 111 or barrel halves. An inner surface 110a of the lower housing half 110 and an inner surface 111a of the upper housing half 111 are semicylindrical, and combined to form the barrel cavity 87 of the cylindrical shape. The barrel cavity 87 is open at both of two ends, which include a first end for containing the first clip 19A and a second end for containing the fastening clip device 18. The exit opening 88 at the first end is open for advancing the multiple clip assembly 13 to the outside of the barrel cavity 87.

The multiple clip assembly 13 is contained in the barrel cavity 87 while the claws 23 of the first clip 19A are open and closed laterally in the horizontal direction. The first clip 19A is set in the closed position by the inside of the barrel cavity 87. As has been described heretofore, the clip devices 17A-17C are oriented with differences in the opening direction of the claws 23 with 90 degrees from one another. There is a difference between the claws 23 and the fins 38 in the opening direction with 90 degrees. Thus, the fins 38 of the tubular shells 20A and 20C are movable for deployment vertically in the depicted state. The fins 38 of the tubular shell 20B are movable for deployment horizontally in the depicted state.

The fin receiving slots 114 are formed in the housing halves 110 and 111 and receive the fins 38 deployed from the tubular shells 20A and 20C. Recesses are formed in edge portions of the housing halves 110 and 111, and define fin receiving slots 115 or skirt receiving slots when joined, so as to receive the fins 38 deployed from the tubular shell 20B. This is effective in setting the fins 38 free from the pressing force toward the stowed position inside the housing 81 in the course of preservation. The force of recovery of the fins 38 toward the deployed position can be kept without lowering. Note that recesses or grooves may be formed in place of through holes or the fin receiving slots 114 and 115.

A receiving cutout 116 is formed at the distal end of the lower housing half 110, and has a width greater than the width of the regulating claw 52 of the support 48. In the introduction of the multiple clip assembly 13 from the housing 81 into the coupling device 82, the regulating claw 52 protrudes from the inside of the barrel cavity 87 through the receiving cutout 116, and prevents over-insertion of the multiple clip assembly 13 into the coupling device 82.

Note that the regulating claw 52 passes one of the fin receiving slots 114 in the introduction of the multiple clip assembly 13 from the housing 81 into the coupling device 82. However, the regulating claw 52 does not enter the fin receiving slot 114 because of its greater width than the fin receiving slot 114. The distal end 52c of the regulating claw 52 does not contact the inside of the barrel cavity 87 owing to the effect of the projection 52b, and does not interfere with the fin receiving slot 114.

A key projection 117 projects from a lower portion of the lower housing half 110, and is positioned in the middle of the housing 81 in the axial direction. A spring arm 117a is included in the key projection 117, and deformable resiliently transversely to the axial direction of the housing 81. A retaining hook 117b of click projects from a lateral surface of the spring arm 117a.

The housing 81 is formed from a transparent plastic material for an operator externally to view the multiple clip assembly 13 inside the barrel cavity 87. To join the upper housing half 111 with the lower housing half 110, it is possible to use adhesive agent for adhesion, ultrasonic waves for welding, claws for engagement and the like. Also, transparent plastic film can be wound on the periphery of the housing obtained by combining the housing halves 110 and 111.

In FIG. 8, a recess 90 is formed in the coupling device 82, and disposed at its end with a reduced height. A stage groove 91 or housing receiving groove is formed in a wall of the recess 90, has an inner diameter slightly greater than an outer diameter of the housing 81, and has an open upper side. An access hole 92 is formed in a wall of the recess 90 and communicates with the stage groove 91.

The housing 81 is inserted in the stage groove 91 and the access hole 92. For the purpose of loading the flexible sheath 11 with the multiple clip assembly 13 from the coupling device 82, the housing 81 is removed from the stage groove 91 and the access hole 92 before inserting the flexible sheath 11 instead. The flexible sheath 11 or the housing 81 inserted in the stage groove 91 appears partially upwards. It is possible to retain the housing 81 and the coupling device 82 or the flexible sheath 11 and the coupling device 82 together by holding in the recess 90.

A connection opening 95 and a wire channel 96 are formed in the upper wall of the coupling device 82 in connection with the recess 90. The connection opening 95 is open for insertion of the shaft head 57 of the operating wire 12 into the coupling device 82 in a lateral direction transverse to a direction in which the housing 81 is inserted in the coupling device 82. An open area of the connection opening 95 is larger than an area of the shaft head 57 as viewed laterally. The wire channel 96 extends for connecting the access hole 92 with the connection opening 95, and has such a dimension as to receive insertion of the operating wire 12 laterally. When the flexible sheath 11 is inserted in the stage groove 91, the operating wire 12 and the shaft head 57 are inserted in the wire channel 96 and the connection opening 95 simultaneously, and become connected with the support 48 of the fastening clip device 18 introduced in the coupling device 82. See FIG. 5.

In FIG. 9, an insertion channel 99 or fin bending channel is formed in the coupling device 82, is positioned inwards from the access hole 92, and has a cylindrical form. The insertion channel 99 has a diameter equal to an inner diameter of the flexible sheath 11 and that of the barrel cavity 87, and internally depresses and stows the fins 38 of the multiple clip assembly 13 introduced from the housing 81.

A regulating contact surface 100 is formed in a step shape, is disposed between the access hole 92 and the insertion channel 99 and near to the end opening of the insertion channel 99, and has a size corresponding to a thickness of the flexible sheath 11 or the housing 81. When an end of the flexible sheath 11 or the housing 81 is set in a firm contact with the regulating contact surface 100, the insertion channel 99 is registered with the inside of the flexible sheath 11 or the housing 81. This is effective in loading the flexible sheath 11 with the multiple clip assembly 13 from the coupling device 82 while the fins 38 are kept depressed and stowed.

The regulating contact surface 100 also operates as a portion engageable with the regulating claw 52 protruding from the barrel cavity 87 through the receiving cutout 116 in the housing 81. See FIG. 19A. Thus, excessive introduction of the support 48 to the inside of the insertion channel 99 can be prevented.

The pull rod structure 83 includes a pull tab 102, a shank 103 and an end connector 104. The pull tab 102 protrudes from the coupling device 82 in its longitudinal direction, and has an elliptic shape. The shank 103 extends from the pull tab 102. The end connector 104 is formed with an end of the shank 103 (See FIG. 11). The shank 103 is inserted in the insertion channel 99 with its length enough for penetration. The end connector 104 is inserted in the barrel cavity 87, and engaged with the first clip 19A.

The pull rod structure 83 is deformed resiliently to depress the annular shape of the pull tab 102 and becomes inserted in the access hole 92 together with the housing 81. The shank 103 is entered in the insertion channel 99. The pull tab 102 comes to protrude to the outside of the coupling device 82 from a pull opening at the end of the insertion channel 99. See the reference numeral 151 in FIG. 18. When the pull tab 102 is pulled relative to the coupling device 82, the first clip 19A of the multiple clip assembly 13 is pulled by the end connector 104 and entered in the insertion channel 99 through the barrel cavity 87.

In FIG. 11, a center channel 103a is formed in the shank 103 of the end connector 104 and disposed near to its end. An anti-reverse projection 103b is formed to project from each of positions higher and lower than the center channel 103a, and extends with an increasing width from the pull tab 102 toward the end connector 104. The anti-reverse projection 103b extends to the outside of the coupling device 82 through the pull opening 151 by deformation of the shank 103 at the center channel 103a with resiliency. The anti-reverse projection 103b retains the shank 103 to prevent its return into the insertion channel 99.

The end connector 104 has an outer diameter equal to that of the tubular shell 20. A pair of guide projections 104a are included in the end connector 104. A wall 104b in the end connector 104 is disposed between the guide projections 104a for keeping their interval. Engageable projections 104c project from lateral surfaces of the wall 104b, and are disposed near to the shank 103.

The end connector 104 is contained in the barrel cavity 87 in the housing 81 with the multiple clip assembly 13. The first clip 19A is kept closed by pressure of the barrel cavity 87. The claws 23 are engaged with the engageable projections 104c. When the pull tab 102 is pulled relative to the coupling device 82, the shank 103 slides in the insertion channel 99 to move the end connector 104 from the barrel cavity 87 into the insertion channel 99.

A release groove 148 is formed to extend horizontally from the insertion channel 99 as illustrated in FIGS. 18A and 18B. The clip 19A, upon reaching the release groove 148, become open with its resiliency and disengaged from the end connector 104. Thus, the multiple clip assembly 13 is set inside the insertion channel 99 in a stationary manner in a state of the fastening mechanism 50 of the fastening clip device 18 positioned in a slide channel 107 in the access hole 92.

In the clip devices 17, an opening direction of the claws 23 is different from a deploying direction of the fins 38 with a difference of 90 degrees. Even when the clip 19A is positioned at the release groove 148, the fins 38 of the tubular shell 20A do not open.

The pull rod structure 83 is one piece molded from plastic material having suitable resiliency, inclusive of the pull tab 102, the shank 103 and the end connector 104. Note that the end connector 104 may be a part separate from the shank 103, and can be joined with the shank 103 inside the coupling device 82.

The stop position of the multiple clip assembly 13 in the coupling device 82 changes according to a time point of disengagement of the clip 19A from the end connector 104. The time point of disengagement of the clip 19A from the end connector 104 is also changeable with various factors, which may be a fastened state between the clip 19A and the end connector 104, an orientation of the clip 19A inside the insertion channel 99, and speed of pulling the pull rod structure 83. In the invention, even when the stop position of the support 48 is offset, the guide surface 170 of the guide slider 84 to be described later can press the contact surface 56 of the support 48 to shift the support 48 suitably.

If the end connector 104 is not disengaged from the clip 19A suitably within the release groove 148, the support 48 may enter the insertion channel 99 so that the shaft head 57 of the operating wire 12 cannot be fastened to the support 48. However, the regulating claw 52 in the invention contacts the regulating contact surface 100 at a point of entry in the insertion channel 99. The support 48 can be prevented from excessive introduction in the insertion channel 99.

The slide channel 107 is formed through a lateral wall of the coupling device 82, and receives insertion of the guide slider 84 in a slidable manner. The guide slider 84 operates when pressed in the slide channel 107 for connecting the fastening clip device 18 introduced in the coupling device 82 with the shaft head 57 inserted through the connection opening 95.

The slide channel 107 extends in a direction perpendicular with the stage groove 91. The slide channel 107 has rectangular form with a width equal to the width of the guide slider 84, and extends in the transverse direction of the coupling device 82.

Figure 12:
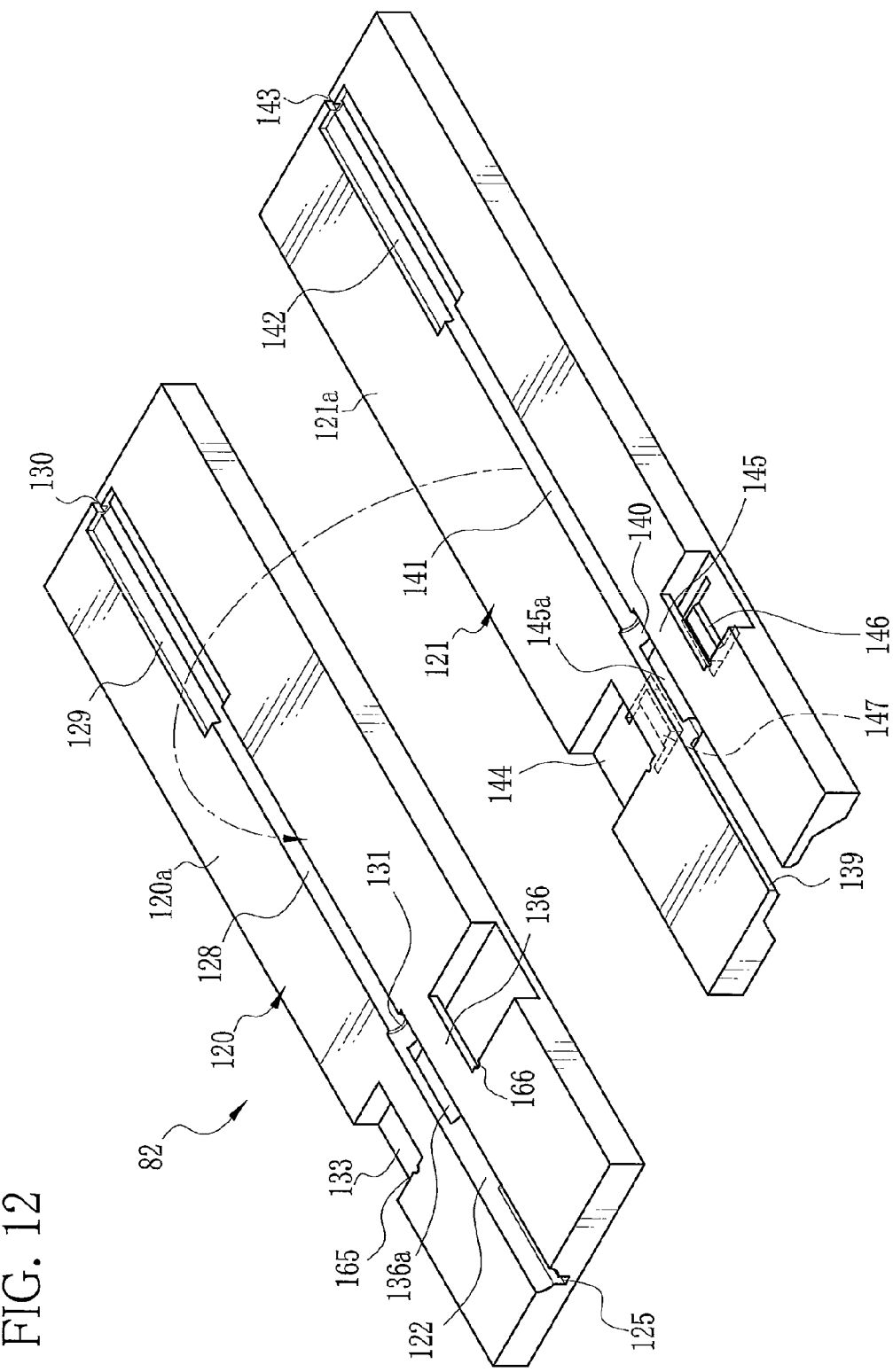
FIG. 12 is an exploded perspective view illustrating a coupling device.

In FIG. 12, the coupling device 82 is constituted by a lower casing 120 and an upper casing 121. An upper surface 120a is defined by the upside of the lower casing 120. An elongated recess 122 is formed in the upper surface 120a, and defines the stage groove 91 and the access hole 92 upon joining the upper casing 121.

A key way groove 125 is formed in the surface of the elongated recess 122. When the housing 81 is inserted in the stage groove 91 and the access hole 92 by advance in the axial direction, the key way groove 125 is engaged with the key projection 117 on the housing 81 for blocking rotation. The engagement of the key projection 117 with the key way groove 125 prevents rotation of the housing 81, and sets the housing 81 in a suitable orientation in the coupling device 82. Also, the engagement of the retaining hook 117b with a retaining opening with a click in the key way groove 125 can notify a user of the status after insertion of the housing 81 to a predetermined position through the access hole 92.

A fin bending recess 128 or skirt bending recess is formed in the lower casing 120, extends from an end of the elongated recess 122, has a semicylindrical shape, and defines the insertion channel 99 when the upper casing 121 is joined. A wall channel 129 for release is formed in an end portion of the lower casing 120, and extends with a greater width from the fin bending recess 128. A rectangular end channel 130 is disposed at an end of the fin bending recess 128, and receives insertion of the shank 103 of the pull rod structure 83.

A stepped bore 131 is disposed at a borderline between the elongated recess 122 and the fin bending recess 128, namely at a proximal end of the fin bending recess 128, and is shaped with a smaller diameter in comparison with an inner surface of the fin bending recess 128. The stepped bore 131 constitutes the regulating contact surface 100, with which the regulating claw 52 is engaged.

A through opening 133 for slide is formed in a lower portion of the elongated recess 122, and constitutes the slide channel 107 when the upper casing 121 is joined, to direct the guide slider 84 to slide transversely to the axial direction of the multiple clip assembly 13. The through opening 133 has a quadrilateral shape, has a width equal to a width of the guide slider 84, and comes through the lower casing 120 transversely to its longitudinal direction.

In the coupling device 82, a bridge portion 136 extends between edge portions of the through opening 133 and is formed in a plate shape. The bridge portion 136 operates for reinforcement with strength at the through opening 133 in the coupling device 82, and is a stopper adapted upon sliding of the guide slider 84 into the slide channel 107. The elongated recess 122 is formed to extend through a part of the bridge portion 136. An access opening 136a is formed through the elongated recess 122 and communicates with the through opening 133.

The upper casing 121 has a lower surface 121a. An elongated slot 139 and an intermediate recess 140 are formed in the lower surface 121a. The elongated slot 139 constitutes the stage groove 91. The intermediate recess 140 has an arcuate shape and constitutes the access hole 92. Also, there are a fin bending recess 141 or skirt bending recess, a wall channel 142 for release, and an end channel 143 formed in the lower surface 121a. The fin bending recess 141 constitutes the insertion channel 99. The end channel 143 is shaped similarly to the end channel 130. The upper casing 121 has a through opening 144 for slide, a bridge portion 145 and an access opening 145a. The through opening 144 constitutes the slide channel 107 near to the intermediate recess 140. The access opening 145a is formed to extend to the connection opening 95 of FIGS. 7A-7D.

Figure 13:
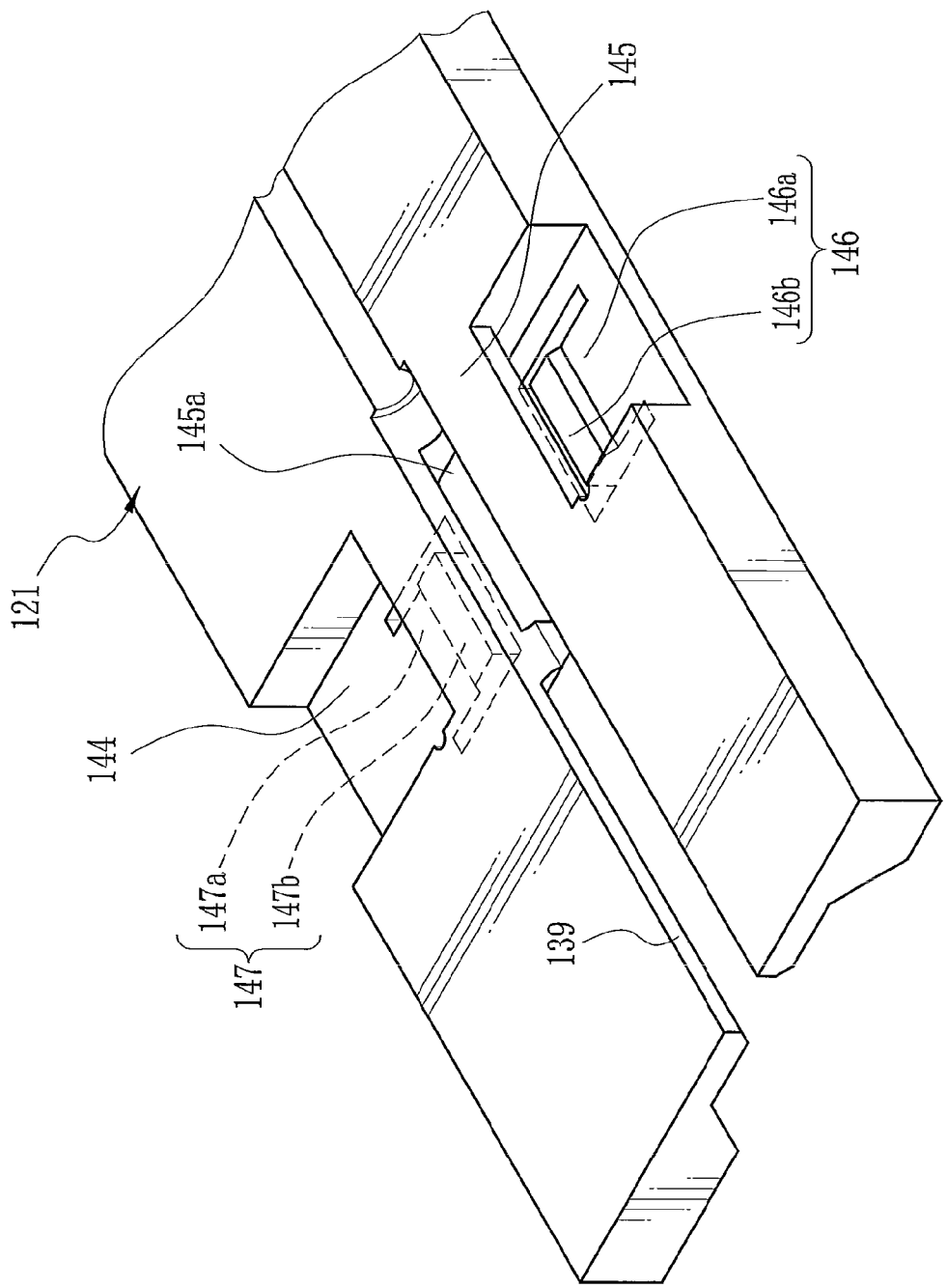
FIG. 13 is an exploded perspective view illustrating elements of the coupling device around a guide slider.

Bias portions 146 and 147 are formed with a wall of the through opening 144, and bias the guide slider 84 in a direction of pressing the shaft head 57 for connection of the shaft head 57 with the support 48 in a guided manner. See FIG. 13. The bias portions 146 and 147 are positioned symmetrically with reference to the access hole 92 or the intermediate recess 140. The bias portions 146 and 147 are constituted by spring plates 146a and 147a and projections 146b and 147b. Each of the spring plates 146a and 147a extends from an end of the upper casing 121 as viewed in its transverse direction toward the center. Each of the projections 146b and 147b projects down from an end of the spring plates 146a and 147a.

In FIGS. 17A-19B, the release groove 148 is defined by a combination of the wall channels 129 and 142, and has a greater width horizontally than the insertion channel 99 upon joining the upper and lower casings 120 and 121. The horizontal width of the release groove 148 is sufficient for allowing the arms 25 of the first clip 19A to open for disengagement from the end connector 104 of the pull rod structure 83. The release groove 148 is so positioned that, when the fastening mechanism 50 of the fastening clip device 18 becomes positioned at the access opening 145a, the first clip 19A reaches the release groove 148. The end channels 130 and 143 define the pull opening 151 in a quadrilateral shape for insertion of the shank 103 of the pull rod structure 83. See FIGS. 17A-19B.

The coupling device 82 is formed from a transparent plastic material for an operator externally to view the multiple clip assembly 13, the housing 81, the pull rod structure 83 and the guide slider 84. To join the upper casing 121 with the lower casing 120, it is possible to use adhesive agent for adhesion, ultrasonic waves for welding, claws for engagement and the like.

Figure 14:
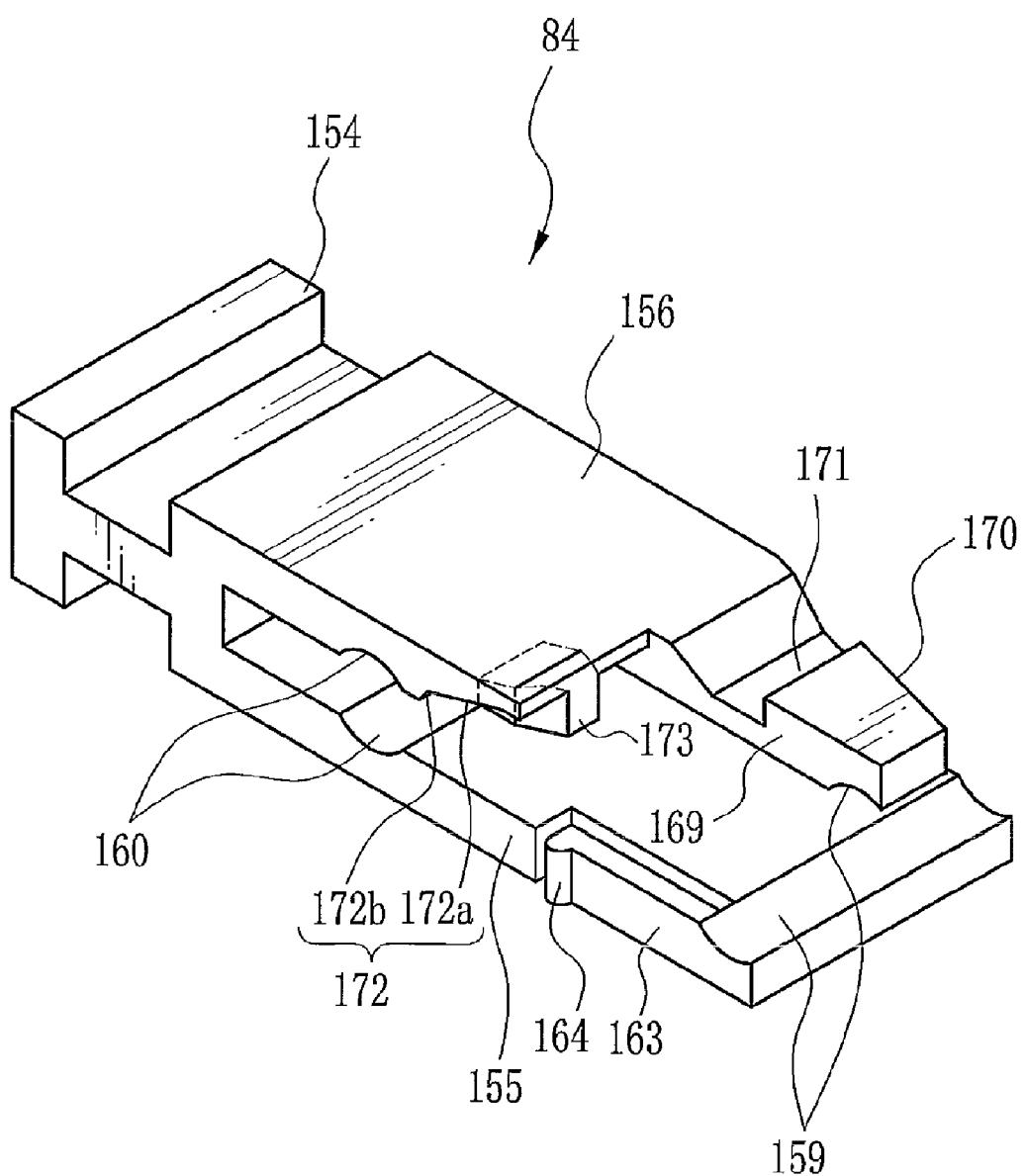
FIG. 14 is a perspective view illustrating the guide slider.

In FIG. 14, the guide slider 84 is one piece molded from a plastic material, and includes a button head 154, a lower slide plate 155 (lower portion) and an upper slide plate 156. The button head 154 is operable for depression into the slide channel 107. The slide plates 155 and 156 are opposed to one another, and extend from the button head 154 horizontally. The slide plates 155 and 156 are inserted in the through openings 133 and 144 of the upper and lower casings 120 and 121, and squeeze the bridge portions 136 and 145.

The guide slider 84 has a smaller size than that of the slide channel 107 for a safely slidable structure. Specifically, an outer size of the upper and lower slide plates 155 and 156 is slightly smaller than an inner size of the through opening 133 and 144. A distance between the upper and lower slide plates 155 and 156 is slightly greater than a thickness of a combination of the bridge portions 136 and 145.

First receiving recesses 159 are formed in inner surfaces of the lower and upper slide plates 155 and 156. Second receiving recesses 160 are also formed and disposed in parallel with the first receiving recesses 159. The first and second receiving recesses 159 and 160 have inner diameters substantially equal to respectively the outer diameters of the flexible sheath 11 and the housing 81. The guide slider 84 is kept slidable between an initial position and a connecting position, and when in the initial position, registers the first receiving recesses 159 with the access hole 92, and when in the connecting position, registers the second receiving recesses 160 with the access hole 92. When the guide slider 84 comes to the connecting position, the bridge portions 136 and 145 of the coupling device 82 contact the inside of the guide slider 84 to prevent its further slide.

The first and second receiving recesses 159 and 160 become registered with the access openings 136a and 145a of the coupling device 82, and constitute portions of the access hole 92. When the housing 81 or the flexible sheath 11 is inserted in the access hole 92, the receiving recesses 159 or 160 receive a peripheral surface of either one of the housing 81 and the flexible sheath 11, to disable the guide slider 84 from sliding.

A spring arm 163 is formed in an end of the lower slide plate 155, and resiliently shiftable in the transverse direction of the guide slider 84. A retaining hook 164 of click projects from an end of the spring arm 163 in the transverse direction of the guide slider 84. Retaining grooves 165 and 166 of click are formed in an edge of the through opening 133 of the lower casing 120. See FIG. 12. The retaining hook 164, when the guide slider 84 is in an initial position, is engaged with the retaining groove 165, and when the guide slider 84 is set in the connecting position, is engaged with the retaining groove 166.

A cutout 169 is formed in the upper slide plate 156 of the guide slider 84 to reduce its width. When the guide slider 84 is in the initial position, the cutout 169 is positioned between the connection opening 95 and the access opening 145a to define a path. Thus, the shaft head 57 can be moved laterally through this path for connection with the support 48.

The upper slide plate 156 has the guide surface 170 oriented opposite to the cutout 169. The guide surface 170 is inclined to increase the plate width in the axial direction in a direction of sliding back of the guide slider 84. While the guide slider 84 advances into the slide channel 107, the guide surface 170 contacts and pushes the contact surface 56 of the support 48 of FIG. 5, and moves the support 48 in the axial direction. Thus, the support 48 is positioned in the axial direction.

When the guide slider 84 becomes pushed in the slide channel 107, a lower end of at least one of the projections 146b and 147b comes in contact with an upper surface (peripheral surface) of the upper slide plate 156. The upper slide plate 156 is pushed in the downward direction by the bias of the spring plates 146a and 147a in contact with the protections 146b and 147b.

The guide slider 84 has such a small size as to be slidable in the slide channel 107. It is likely that the guide slider 84 shifts (pitches) horizontally or perpendicularly to the sliding direction with play, and also shifts vertically with play. The spring plates 146a and 147a bias the guide slider 84 downwards when the guide slider 84 is slid in through the slide channel 107, to prevent the guide slider 84 from unstably shifting within the slide channel 107. Thus, the upper slide plate 156 of the guide slider 84 can contact the shaft head 57 reliably for depression in a downward direction.

A recess 171 is formed in the upper surface of the upper slide plate 156 for containing the projection 146b. The recess 171, when the guide slider 84 is in the initial position, sets the upper surface of the upper slide plate 156 away from the projection 146b to prevent interference. See FIG. 15A. The projection 147b is internally distant from the front end of the upper slide plate 156. The upper slide plate 156 does not contact the projections 146b and 147b and is not biased by the spring plates 146a and 147a when the guide slider 84 is in the initial position.

A shifting wall 172 is a lower wall of the upper slide plate 156, presses the shaft head 57 in the access hole 92 through the access opening 145a when slid from the initial position to the connecting position, for the support 48 to hook the shaft head 57 in the fastening clip device 18. The shifting wall 172 includes a first inclined surface 172a and a second inclined surface 172b. The first inclined surface 172a extends downwards from the cutout 169 toward the second receiving recesses 160 with reference to the slide of the guide slider 84. The second inclined surface 172b extends downwards from the first inclined surface 172a toward the second receiving recesses 160 with a greater angle than the first inclined surface 172a.

As has been described heretofore, the guide slider 84 is inserted in the slide channel 107, of which an inner surface supports the shifting wall 172 by contact with the upper slide plate 156. Reaction force in pressing the shaft head 57 with the shifting wall 172 is received by the slide channel 107. Thus, deformation of the guide slider 84 and changes in its orientation can be prevented.

The shifting wall 172 is effective in pressing the shaft head 57, as the shifting wall 172 is inclined with reference to a sliding direction of the guide slider 84 and with a gradual increase of a shift amount of the shaft head 57 of the push with the shifting wall 172. A direction of pressure to the shaft head 57 is varied with reference to the sliding direction of the guide slider 84 before the shaft head 57 can be fastened to the support 48. The shift amount can be somewhat smaller in consideration of a sliding distance of the guide slider 84.

The shifting wall 172 is constituted by the first and second inclined surfaces 172a and 172b. The first inclined surface 172a operates in an initial phase of shifting with the guide slider 84 for pressing the shaft head 57 into the support 48 with a smaller shift amount relative to the sliding distance of the guide slider 84. After the initial phase, the second inclined surface 172b operates for pressing the shaft head 57 into the support 48 finally to obtain a fastened state with a greater shift amount relative to the sliding distance of the guide slider 84.

A pushing portion 173 is formed with a lower surface of the upper slide plate 156 to project from the first inclined surface 172a downwards. The pushing portion 173 has a wedge shape with an increasing width in the axial direction of the operating wire 12 with respect to a direction of sliding back of the guide slider 84. When the guide slider 84 moves from the initial position to the connecting position, the pushing portion 173 comes between the front and rear shaft head portions 58 and 59. The pushing portion 173 depresses a portion of the operating wire 12 between the front and rear shaft head portions 58 and 59, and tightens the fastened state by pressure to the operating wire 12 as well as the shaft head 57. The pushing portion 173 can position the front and rear shaft head portions 58 and 59 in the axial direction by contacting those with lateral faces in the position between the front and rear shaft head portions 58 and 59.

The lower slide plate 155, when inserted in the slide channel 107, is opposed to the shifting wall 172 in the presence of the support 48 and the shaft head 57 between those, and operates to support the support 48 and the shaft head 57 pressed by the shifting wall 172. Thus, fastening with the support 48 or the shaft head 57 can be stable without looseness.

Figure 15A:
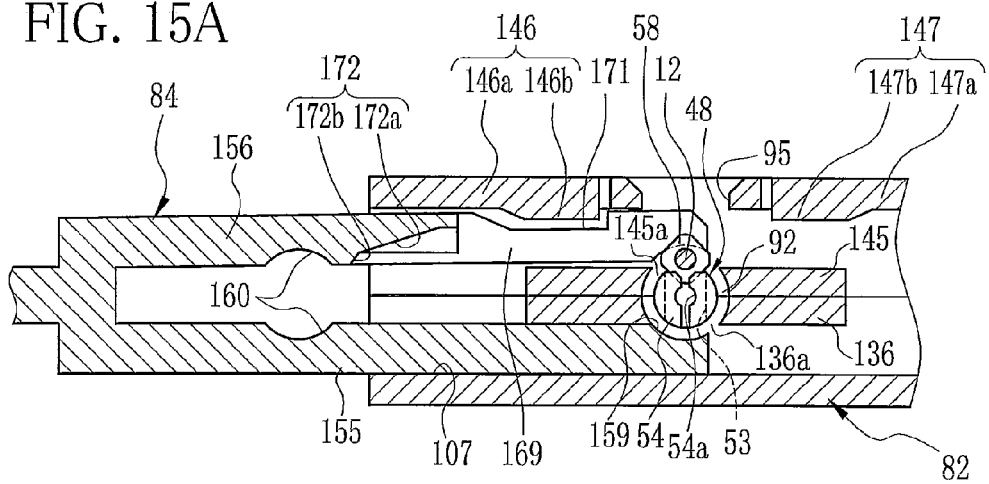
FIG. 15A is a cross section illustrating bias of a bias portion to the guide slider.

A process of fastening the shaft head 57 of the operating wire 12 to the support 48 of the multiple clip assembly 13 in the coupling device 82 is described by referring to FIGS. 15A-17B. In FIG. 15A, the guide slider 84 is in the initial position. The shaft head 57 is inserted in the connection opening 95 laterally, so as to insert corners of the lateral surface 58a of the front shaft head portion 58 between the cavity walls 53 of the support 48 through the access opening 145a. The projection 146b is in the recess 171 when the guide slider 84 is in the initial position. The guide slider 84 is not biased by the spring plates 146a and 147a as the projections 146b and 147b do not contact the upper slide plate 156. The guide slider 84 is loose with play inside the slide channel 107. It is likely in FIG. 15A that the upper slide plate 156 is unstable relative to the bridge portion 145 in the upward direction.

Figure 15B:
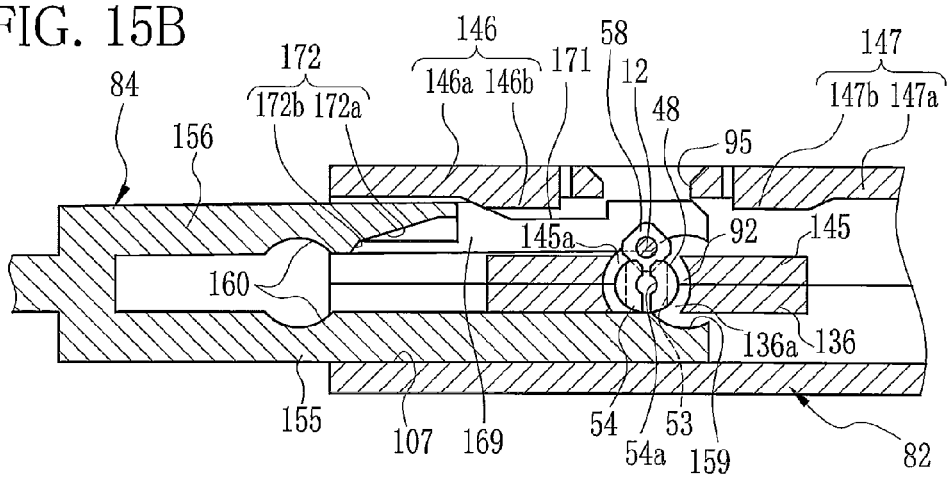
FIG. 15B is a cross section illustrating a step of insertion of a shaft head into a fastening mechanism.

In FIG. 15B, the projection 146b contacts a proximal end of the recess 171 upon sliding of the guide slider 84 into the slide channel 107 from the initial position. The guide slider 84 is further slid with pressure from the position of the contact of the projection 146b with the recess end. The projection 146b becomes offset from the recess 171 and comes in contact with the upper surface of the upper slide plate 156. The spring plate 146a with resiliency biases the upper slide plate 156 downwards by the contact of the projection 146b. This is effective in reducing the play of the guide slider 84 and preventing the upper slide plate 156 from being unstable in the upward direction.

Figure 17A:
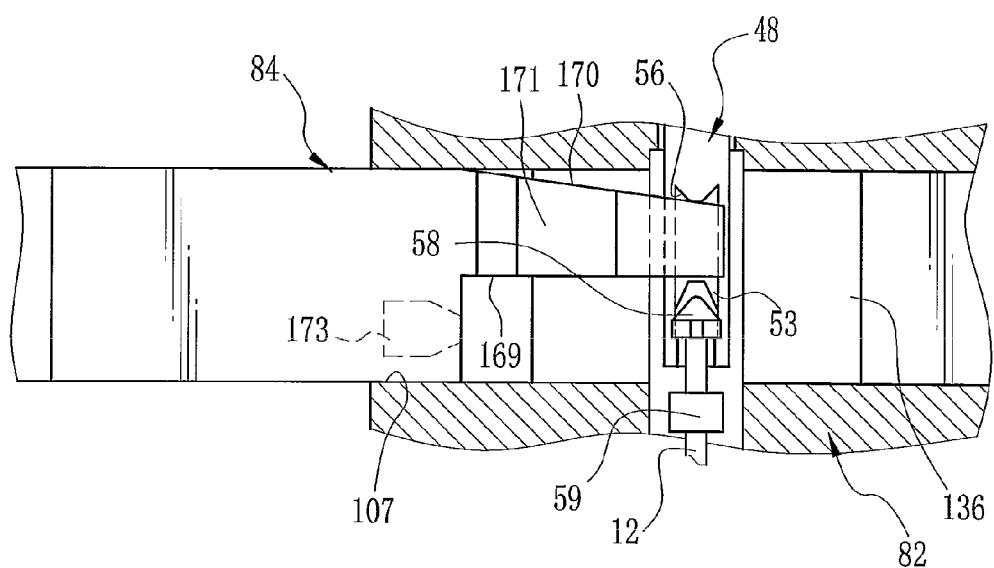
FIG. 17A is a horizontal section illustrating a state of positioning the support for the fastening clip and the operating wire with the guide slider.

When the guide slider 84 is slid into the slide channel 107, the guide surface 170 of the upper slide plate 156 contacts the contact surface 56 of the support 48 as depicted in FIG. 17A. As the guide surface 170 is inclined in the axial direction of the multiple clip assembly 13 as viewed in the sliding direction. When the guide slider 84 is set inside the slide channel 107, the guide surface 170 pushes the contact surface 56 in the axial direction. Thus, the support 48 is moved to the connecting position for fastening to the shaft head 57. As has been described heretofore, the support 48 may be positioned incidentally at a point behind a suitable position for fastening of the shaft head 57 as viewed in the axial direction when the multiple clip assembly 13 is introduced in the coupling device 82 by pulling the pull tab 102. However, the guide surface 170 pushes the contact surface 56 according to the invention, so as to move the support 48 to the suitable position for fastening of the shaft head 57.

Figure 15C:
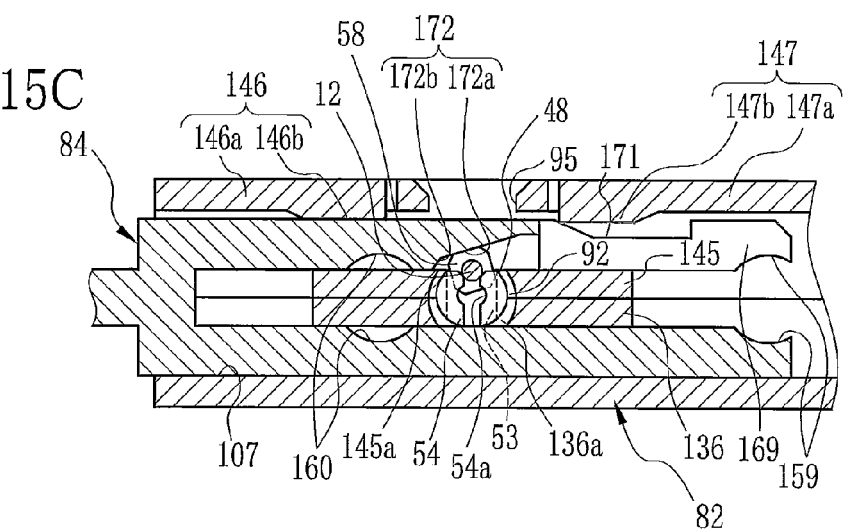
FIG. 15C is a cross section illustrating a step of fastening by use of a first inclined surface of the guide slider.

In FIG. 15C, the guide slider 84 is pushed further inwards through the slide channel 107. The upper slide plate 156 is biased downwards by the spring plate 146a with resiliency. The first inclined surface 172a of the shifting wall 172 comes in contact with the front and rear shaft head portions 58 and 59. As play of the guide slider 84 is reduced by the bias of the upper slide plate 156 in the downward direction, the shifting wall 172 reliably comes in contact with the front and rear shaft head portions 58 and 59, and presses those down gradually. Should there be play with the guide slider 84 and should the upper slide plate 156 pass the connecting position in a loosely set condition, the shifting wall 172 does not sufficiently contact the front and rear shaft head portions 58 and 59, so that an error in fastening may occur between the shaft head 57 and the support 48. However, in the present invention, the play of the guide slider 84 is effectively reduced by the bias of the bias portion 146. It is possible to press the guide slider 84 reliably with a suitable shift by contact of the shifting wall 172 with the front and rear shaft head portions 58 and 59.

Figure 17B:
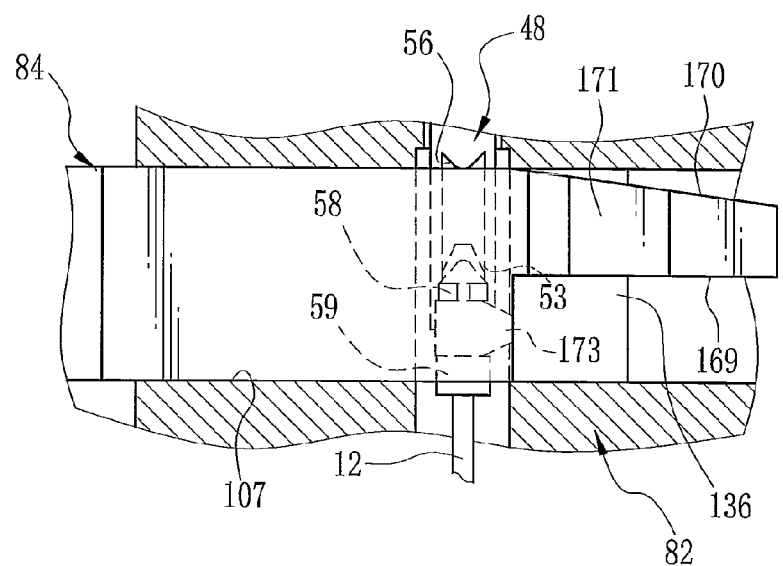
FIG. 17B is a horizontal section illustrating a state of sliding the guide slider after the state of FIG. 17A.

As illustrated in FIG. 17B, the pushing portion 173 advances between the front and rear shaft head portions 58 and 59. The operating wire 12 is pushed down by the pushing portion 173. Also, lateral faces of the pushing portion 173 contact the front and rear shaft head portions 58 and 59, so as to position the shaft head 57 in the axial direction easily. The lateral surface 58a of the front shaft head portion 58 rotates according to the first inclined surface 172a, deforms the cavity walls 53 resiliently, and becomes clamped between those. Also, the operating wire 12 is thrust between the clamping walls 54 by spreading laterally.

The shifting wall 172 is caused by slide of the guide slider 84 to create friction in contact with the shaft head 57. In the present invention, the first inclined surface 172a with a smaller inclination is used at first for shifting while the force of engagement between the support 48 and the shaft head 57 is small. Errors in the connection by offsetting of the shaft head 57 from the support 48 in the sliding direction are prevented, the first inclined surface 172a causing a smaller force component of the force of sliding in the horizontal direction. In the course of the engagement, resistance to the horizontal force component occurs. Then the second inclined surface 172b with a greater inclination is used for shifting finally to fasten the shaft head 57 with the support 48, the second inclined surface 172b being so formed that a ratio of the shift amount of the push to the sliding distance is higher than that of the first inclined surface 172a.

It is likely that offsetting occurs with the operating wire 12 or the support 48 to cause failure in fastening if the operating wire 12 and the shaft head 57 are pressed into the fastening mechanism 50 abruptly. However, it is possible in the invention to reduce occurrence of abnormal fastening because the shaft head 57 is entered gradually by the first inclined surface 172a having a small inclination.

Figure 16A:
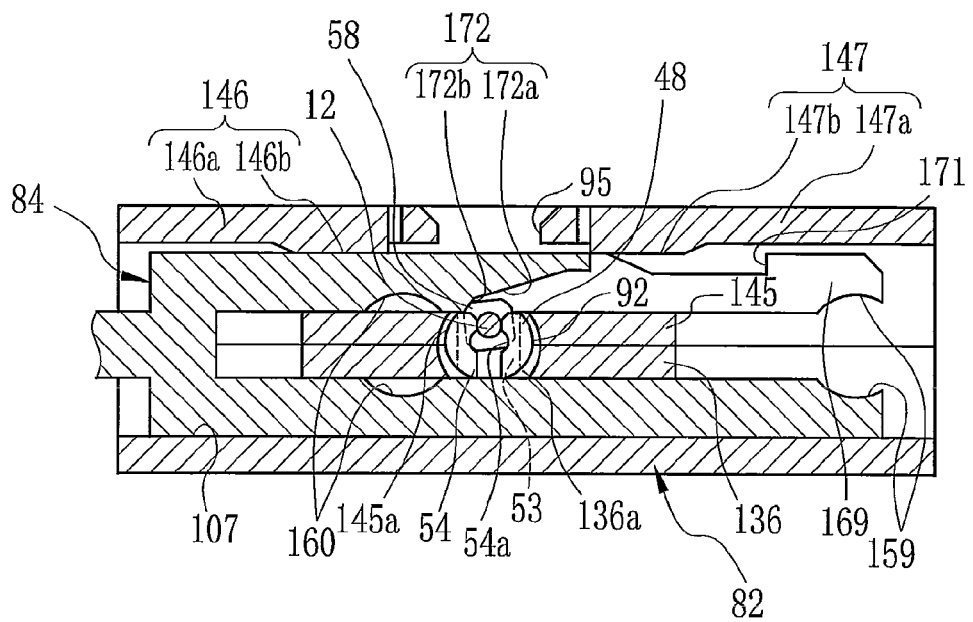
FIG. 16A is a cross section illustrating bias of the bias portion to the guide slider, and fastening of the shaft head to the fastening mechanism by use of a second inclined surface of the guide slider.
Figure 16B:
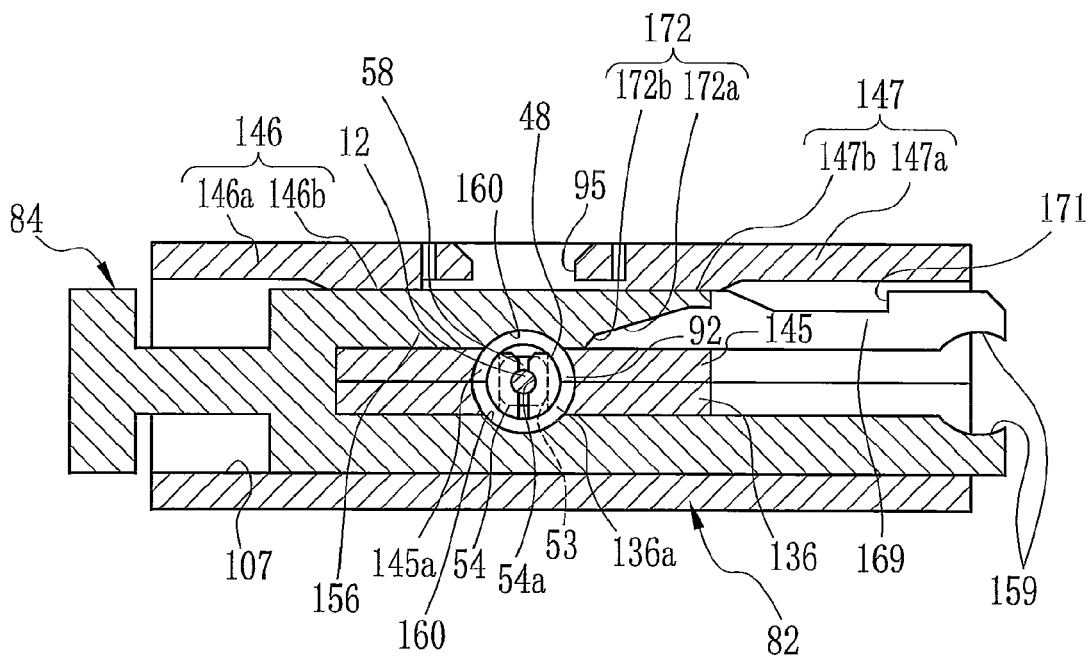
FIG. 16B is a cross section illustrating a fastened state of the shaft head to the fastening mechanism.

In FIG. 16A, the second inclined surface 172b pushes the shaft head portions 58 and 59 quickly downwards in response to the slide of the guide slider 84. The projection 147b as well as the projection 146b comes in contact with the upper surface of the upper slide plate 156, which is biased down by resiliency of the spring plates 146a and 147a. Thus, the pressure to the front and rear shaft head portions 58 and 59 is increased. In FIG. 16B, the front shaft head portion 58 becomes inserted between the cavity walls 53. The operating wire 12 becomes clamped between the clamping walls 54. The rear shaft head portion 59 comes in contact with a proximal end of the clamping walls 54.

When the housing 81 is pulled out of the coupling device 82, the fastening mechanism 50 of the support 48 is unstable within the access hole 92. However, the lower slide plate 155 of the guide slider 84 receives a lower portion of the fastening mechanism 50 through the access opening 136a, and can keep the fastening mechanism 50 positioned firmly even with pressure of the shifting wall 172. The upper and lower slide plates 155 and 156 of the guide slider 84 are retained by the coupling device 82, and can be prevented from deformation even upon reaction in the course of hooking the shaft head 57 on the support 48.

FIGS. 18-21 are referred to now, to describe loading of the multiple clip assembly 13 from the multiple clip package 80 in the flexible sheath 11.

At first, the housing 81 and the coupling device 82 in FIG. 8 are held together by the recess 90. The pull tab 102 is pulled from the coupling device 82. The end connector 104 is slid to the insertion channel 99 by following the shank 103 pulled through the coupling device 82. The multiple clip assembly 13 is introduced in the insertion channel 99 through the barrel cavity 87 by the pull of the end connector 104.

In FIG. 18A, the multiple clip assembly 13 is introduced in the insertion channel 99. The fins 38 of the tubular shell 20 are depressed and stowed by the inside of the insertion channel 99. When the clip 19A reaches the release groove 148, the arms 25 of the clip 19A become open to disengage the claws 23 from the end connector 104. The multiple clip assembly 13 is now stationary at a predetermined point in the insertion channel 99. The support 48 of the fastening clip device 18 reaches the position corresponding to the connection opening 95. The pull rod structure 83 is pulled until the anti-reverse projection 103b comes to protrude from the coupling device 82 externally.

If failure occurs in releasing the clip 19A and the end connector 104 within the release groove 148, then the regulating claw 52 comes to protrude from the barrel cavity 87 through the receiving cutout 116 of the housing 81 and becomes engaged with the regulating contact surface 100. See FIG. 19A. Thus, the support 48 is positioned in a stationary state in correspondence with the connection opening 95 without excessive introduction in the insertion channel 99.

In FIG. 18B, the housing 81 is removed from the access hole 92 in the axial direction. Then a portion of the support 48 appears after exiting from the access hole 92. The fastening mechanism 50 of the support 48 becomes opposed to the connection opening 95 through the slide channel 107.

The operating wire 12 and the shaft head 57 initially protrude from the sheath end of the flexible sheath 11 by pull of the sheath handle 63 relative to the wire handle 62. In FIG. 20A, the flexible sheath 11, the operating wire 12 and the shaft head 57 are inserted downwards to the coupling device 82 respectively toward the stage groove 91, the wire channel 96 and the connection opening 95. After the insertion of the flexible sheath 11, the flexible sheath 11 and the coupling device 82 are retained together by use of the recess 90. Corners of the lateral surface 58a of the front shaft head portion 58 are inserted between the cavity walls 53.

When the guide slider 84 is slid through the slide channel 107, the first and second inclined surfaces 172a and 172b of the shifting wall 172 depress the front and rear shaft head portions 58 and 59 downwards by reducing play of the guide slider 84 to prevent its error. See FIGS. 15A-16B. The guide surface 170 presses the contact surface 56 to position the support 48. At the same time, the pushing portion 173 comes into a gap between the front and rear shaft head portions 58 and 59 to depress the operating wire 12, and positions the shaft head 57 in the axial direction. Owing to the positioning and reduction of the play, the front shaft head portion 58 pushed by the guide slider 84 can be inserted between the cavity walls 53 as illustrated in FIG. 20B. Also, the operating wire 12 becomes clamped between the clamping walls 54. The rear shaft head portion 59 contacts a proximal end of the clamping walls 54.

Figure 21A:
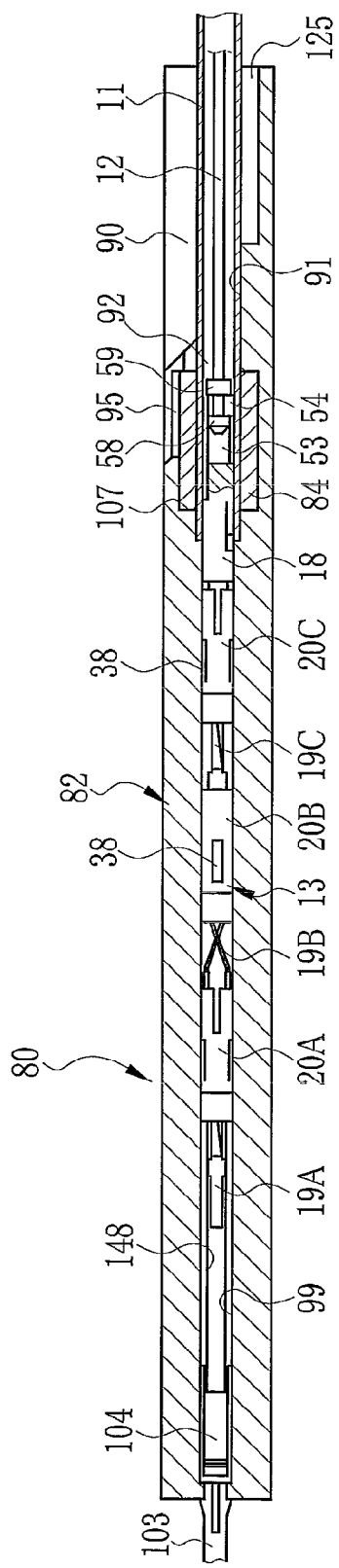
FIGS. 21A and 21B are vertical sections illustrating states of introducing the multiple clip assembly from the coupling device into a flexible sheath.

In FIG. 21A, the flexible sheath 11 is advanced relative to the operating wire 12, to insert the flexible sheath 11 in the access hole 92. The sheath end of the flexible sheath 11 comes in contact with the regulating contact surface 100. In FIG. 19B, the support 48 is inserted in the flexible sheath 11 to depress the regulating claw 52 inside the flexible sheath 11. Then the operating wire 12 is pulled relative to the flexible sheath 11. For example, the wire handle 62 is pulled away from the sheath handle 63, so that the operating wire 12 can be moved relative to the flexible sheath 11 with a great length.

Figure 21B:
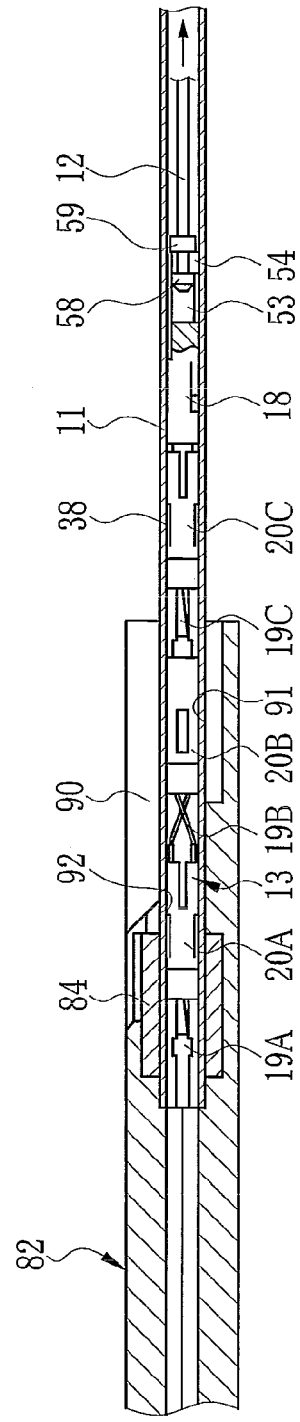

In FIG. 21B, the operating wire 12 is pulled. In response, the multiple clip assembly 13 is introduced in the flexible sheath 11 by advance of its proximal end. As the inner surface of the flexible sheath 11 is registered with the insertion channel 99 during loading of the multiple clip assembly 13, the multiple clip assembly 13 can be moved while the fins 38 are depressed, so that the resistance can be reduced. The multiple clip assembly 13 can be loaded in the flexible sheath 11 without offsetting of the tubular shells 20A-20C from the clips 19A-19C.

When the sheath handle 63 is engaged with the first one of the notches 69 of the wire handle 62, loading of the multiple clip assembly 13 is completed. The flexible sheath 11 with the multiple clip assembly 13 is pulled away from the coupling device 82.

As has been described heretofore, it is possible in the multiple clip package 80 to preserve and handle the shaft head 57 is engaged with the support 48 by sliding the guide slider 84 in the multiple clip package 80, which can be operated easily. As the shaft head 57 is gradually shifted by the guide slider 84 for engagement with the support 48, offsetting of the shaft head 57 from the support 48 can be prevented. A shift amount of the shaft head 57 with the guide slider 84 increases gradually according to angles of the first and second inclined surfaces 172a and 172b of the shifting wall 172, so that handling of the guide slider 84 can be stable without dependency of an operator's manual skill. As the upper slide plate 156 of the guide slider 84 is biased down by the bias portions 146 and 147, failure in guiding of the guide slider 84 can be prevented. Furthermore, the pushing portion 173 enters the gap between the front and rear shaft head portions 58 and 59 to depress the operating wire 12, so as to tighten the fastened state between the support 48 and the shaft head 57.

As the guide surface 170 shifts the support 48 in the axial direction by pressure to the contact surface 56, the support 48 can be adjusted in a suitable position. Engagement of the regulating claw 52 with the regulating contact surface 100 makes it possible to prevent the support 48 from excessive introduction into the insertion channel 99.

In the above embodiment, the guide slider 84 pushes the shaft head 57 for engagement with the support 48. However, the support 48 may be pushed by the guide slider 84 for engagement with the shaft head 57. In the above embodiment, a structure for fastening includes the fastening clip 47 engageable with the proximal end of the clip 19 and the support 48 for retaining the fastening clip 47. However, a structure for fastening can be engaged directly with a proximal end of the clip 19 without use of a fastening clip or dummy clip.

In the above embodiments, the slider is pushed through one lateral side of the coupling device. However, a slider may be pushed through both lateral sides of the coupling device or the clip containing housing, so as to press a first one of the support 48 and the shaft head 57 toward a remaining one of those.

In the above embodiments, the housing 81 is cylindrical. The coupling device 82 has a box shape or plate shape. However, the housing 81 and the coupling device 82 can be formed in other shapes. In the above embodiments, the multiple clip package is for use with a hemostatic clip application apparatus of a multiple type. However, a clip package of the invention may contain one clip device and may be for use with a hemostatic clip application apparatus of a single shot type.

In the above embodiment, the regulating claw 52 is formed as a portion of the support 48. Furthermore, the regulating claw 52 may be formed on any one of various parts included in a multiple clip assembly in a form near to the regulating claw 52 according to the embodiment.

The invention is not limited to the above embodiments of the multiple clip package and clip coupling method. Various alterations and modifications are possible in the scope of the invention. Furthermore, an endoscope for use with the multiple clip application apparatus of the invention may be a rigid endoscope instead of a flexible endoscope.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A clip package for containing a clip device for use with a clip application apparatus and for loading said clip application apparatus with said clip device, comprising:
   a clip assembly, including said clip device, and a fastening mechanism, disposed at a proximal end of said clip device, for fastening to a shaft head of an operating wire inserted through a flexible sheath of said clip application apparatus;
   a coupling device, including a casing for containing said clip assembly in a manner movable from said fastening mechanism toward said flexible sheath, and a guide mechanism for pressing at least one of said fastening mechanism and said shaft head toward a remaining one thereof, for fastening thereof, said fastening mechanism emerging from said casing, said shaft head being overlapped on said fastening mechanism in an axial direction of said clip assembly;
   wherein said guide mechanism is slidable in a sliding direction transverse to said axial direction of said clip assembly, and includes a shifting wall for pressing said at least one of said shaft head and said fastening mechanism upon sliding, and said shifting wall is so inclined as to increase shift of said at least one of said shaft head and said fastening mechanism gradually upon sliding said guide mechanism;
   wherein said shifting wall includes a first inclined surface for initially contacting said at least one of said fastening mechanism and said shaft head upon sliding of said guide mechanism, and a second inclined surface for contacting said at least one of said fastening mechanism and said shaft head after contact of said first inclined surface, and an angle of an inclination of said first inclined surface is smaller than an angle of an inclination of said second inclined surface as viewed in said sliding direction of said guide mechanism.

2. A clip package as defined in claim 1, wherein said coupling device has a slide channel for receiving said guide mechanism in a slidable manner, and an inner surface of said slide channel supports said shifting wall.

3. A clip package as defined in claim 2, wherein said slide channel has a bias portion for biasing said shifting wall in a pressing direction while said shifting wall presses said at least one of said fastening mechanism and said shaft head upon sliding said guide mechanism.

4. A clip package as defined in claim 3, wherein said bias portion is a resiliently deformable spring plate, formed with an inner surface of said slide channel, and having a free end, and a projection is disposed to project from said free end, for contacting a peripheral surface of said guide mechanism to bias said shifting wall in said pressing direction.

5. A clip package as defined in claim 4, wherein said peripheral surface of said guide mechanism has a recess or opening for defining a distance from said projection to prevent interference when said guide mechanism is in an initial position prior to a start of sliding.

6. A clip package as defined in claim 5, wherein said guide mechanism includes a lower portion, opposed to said shifting wall in presence of said fastening mechanism and said shaft head, for supporting said fastening mechanism and said shaft head pressed by said shifting wall.

7. A clip package as defined in claim 6, wherein said guide mechanism includes a pushing portion for pushing a portion of said operating wire upon pressing of said shifting wall to said at least one of said fastening mechanism and said shaft head.

8. A clip package as defined in claim 7, wherein said pushing portion projects from said shifting wall in said pressing direction, and has a wedge form of which lateral sides are inclined to spread in said axial direction, said pushing portion enters said shaft head between plural shaft head portions thereof upon sliding said guide mechanism, to position said shaft head in said axial direction by contact of said lateral sides with said shaft head portions.

9. A clip package as defined in claim 8, wherein said coupling device is adapted to loading said flexible sheath with said clip assembly;
said coupling device has a stage portion for connection of a housing for containing said clip assembly;
said casing includes an insertion channel for receiving introduction of said clip assembly by advance of a distal end thereof from said housing shortly before loading in said flexible sheath.

10. A clip package as defined in claim 9, wherein said guide mechanism includes a receiving portion, engaged with said housing connected with said coupling device, for preventing removal of said guide mechanism from said coupling device.

11. A clip package as defined in claim 1, wherein said guide mechanism includes a guide portion, engaged with said fastening mechanism before pushing said at least one of said fastening mechanism and said shaft head, for positioning said fastening mechanism in said axial direction.

12. A clip package as defined in claim 11, wherein said guide portion is a guide surface so inclined as to increase a width thereof in said axial direction with reference to a backward direction of sliding.

13. A clip package as defined in claim 12, wherein said fastening mechanism has a rod shape, and has a contact surface, positioned erectly in a radial direction from a peripheral surface thereof, for engagement with said guide surface.

14. A clip package for containing a clip device for use with a clip application apparatus and for loading said clip application apparatus with said clip device, comprising:
a clip assembly, including said clip device, and a fastening mechanism, disposed at a proximal end of said clip device, for fastening to a shaft head of an operating wire inserted through a flexible sheath of said clip application apparatus;
a housing for containing said clip assembly in a manner movable by advance of a distal end thereof;
a coupling device, including a stage portion for connection of said housing, and an insertion channel for receiving introduction of said clip assembly by advance of said distal end from said housing, so as to load said flexible sheath with said clip assembly;
a regulating claw disposed to project from said clip assembly outwards and transversely to an axial direction thereof when said clip assembly is pulled from said housing;
a regulating portion, disposed on said coupling device, for engagement with said regulating claw to regulate introduction of said fastening mechanism into said insertion channel;
a guide mechanism for pressing at least one of said fastening mechanism and said shaft head toward a remaining one thereof, for fastening by applying pressure thereto, said shaft head being overlapped on said fastening mechanism in an axial direction of said clip assembly, wherein the guide mechanism is slidable in a sliding direction transvers to the axial direction of the clip assembly.

15. A clip package as defined in claim 14, wherein said regulating portion has a regulating contact surface disposed near to an end opening of said insertion channel in a step shape.

16. A clip package as defined in claim 15, wherein said regulating claw projects when a distal end thereof resiliently deploys about a proximal end thereof secured to said fastening mechanism, and is engaged with said regulating portion.

17. A clip package as defined in claim 16, wherein said regulating claw is formed with said fastening mechanism by way of one piece.

18. A clip package as defined in claim 17, further comprising a projection, disposed on an outer surface of said regulating claw, for reducing friction created on a surface contacting said regulating claw during movement of said clip assembly.

19. A clip package as defined in claim 14 wherein said fastening mechanism is positioned in a connecting position by engagement between said regulating claw and said regulating portion, for said guide mechanism to fasten said shaft head to said fastening mechanism.

* * * * *